US009943500B2

(12) United States Patent
Page

(10) Patent No.: US 9,943,500 B2
(45) Date of Patent: Apr. 17, 2018

(54) METHODS OF TREATING TOPICAL MICROBIAL INFECTIONS

(71) Applicant: LUODA PHARMA PTY LIMITED, Caringbah (AU)

(72) Inventor: Stephen Page, Newtown (AU)

(73) Assignee: Luoda Pharma Pty Ltd, Caringbah (AU)

( * ) Notice: Subject to any disclaimer, the term of this patent is extended or adjusted under 35 U.S.C. 154(b) by 0 days.

(21) Appl. No.: 14/766,232

(22) PCT Filed: Feb. 10, 2014

(86) PCT No.: PCT/AU2014/000101
§ 371 (c)(1),
(2) Date: Aug. 6, 2015

(87) PCT Pub. No.: WO2014/121342
PCT Pub. Date: Aug. 14, 2014

(65) Prior Publication Data
US 2016/0000748 A1 Jan. 7, 2016

(30) Foreign Application Priority Data

Feb. 8, 2013 (AU) .............................. 2013900412

(51) Int. Cl.
| | | |
|---|---|---|
| *A61K 31/352* | (2006.01) | |
| *A61K 31/35* | (2006.01) | |
| *A61K 31/351* | (2006.01) | |
| *A61K 31/7048* | (2006.01) | |
| *A61K 9/06* | (2006.01) | |
| *A61K 9/00* | (2006.01) | |
| *A61K 45/06* | (2006.01) | |
| *A61K 47/06* | (2006.01) | |
| *A61K 47/10* | (2017.01) | |
| *A61K 47/14* | (2017.01) | |
| *A61K 47/44* | (2017.01) | |
| *A61L 15/46* | (2006.01) | |
| *A61L 26/00* | (2006.01) | |

(52) U.S. Cl.
CPC .......... *A61K 31/352* (2013.01); *A61K 9/0014* (2013.01); *A61K 9/0017* (2013.01); *A61K 9/0043* (2013.01); *A61K 9/0046* (2013.01); *A61K 9/0048* (2013.01); *A61K 9/06* (2013.01); *A61K 31/35* (2013.01); *A61K 31/351* (2013.01); *A61K 31/7048* (2013.01); *A61K 45/06* (2013.01); *A61K 47/06* (2013.01); *A61K 47/10* (2013.01); *A61K 47/14* (2013.01); *A61K 47/44* (2013.01); *A61L 15/46* (2013.01); *A61L 26/0066* (2013.01); *A61L 2300/404* (2013.01)

(58) Field of Classification Search
CPC .... A61K 31/35; A61K 31/351; A61K 31/352; A61K 31/7048; A61K 45/06; A61K 9/0014; A61K 9/0017; A61K 9/0043; A61K 9/0046; A61K 9/06; A61K 47/10; A61K 47/14; A61K 47/44; A61K 9/0048; A61K 47/06; A61L 15/46; A61L 2300/404; A61L 26/0066
See application file for complete search history.

(56) References Cited

U.S. PATENT DOCUMENTS

| | | | | |
|---|---|---|---|---|
| 3,873,693 A | | 3/1975 | Meyers et al. | |
| 3,920,847 A | * | 11/1975 | Chalaust | ............... A61K 9/0014 514/512 |
| 4,772,470 A | * | 9/1988 | Inoue | ..................... A61K 9/006 424/435 |
| 2005/0187199 A1 | * | 8/2005 | Peyman | ................... A61K 8/36 514/154 |

FOREIGN PATENT DOCUMENTS

| | | |
|---|---|---|
| EP | 0294538 A2 | 12/1988 |
| WO | WO-2003/088965 A1 | 10/2003 |
| WO | WO-2006/081327 A2 | 8/2006 |
| WO | WO-2008/075207 A2 | 6/2008 |

OTHER PUBLICATIONS

Weese et. al., Veterinary Microbiology, 2010, Elsevier, vol. 140, pp. 418-429.*
Brindle, Encyclopedia of Chemical Technology. Polyether antibiotics, Nov. 2013, Wiley, Abstract and pp. 1-30.*
Huczynski et. al., Journal of Molecular Structure, 2008, Elsevier, vol. 891, pp. 481-490.*
Chen et. al., Journal of Medicinal Chemistry, 2001, American Chemical Society, vol. 44, pp. 2374-2377.*
Dykhuizen, Antonie van Leeuwenhoek, 1998, Kluwer Academic Publishers, vol. 73, pp. 25-33.*
Foroumadi et. al., European Journal of Medicinal Chemistry, 2003, Elsevier, vol. 38, pp. 851-854.*
Lu-Lu et. al., Infection and Immunity, 1992, American Society for Microbiology, vol. 60(9), pp. 3807-3813.*
Akiyama et al., *Staphylococcus aureus* infection on experimental croton oil-inflamed skin in mice. *Staphylococcus aureus* infection on experimental croton oil-inflamed skin in mice. *J. Dermatol. Sci.* 8(1): 1-10 (1994).
Gilbert et al., The 10×'20 Initiative: pursuing a global commitment to develop 10 new antibacterial drugs by 2020. *Clin. Infect. Dis.* 50(8): 1081-3 (2010).
Guo et al., In vivo bioluminescence imaging to evaluate systemic and topical antibiotics against community-acquired methicillin-resistant *Staphylococcus aureus*-infected skin wounds in mice. *Antimicrob. Agents Chemother.* 57(2): 855-63 (2013).
International Search Report and Written Opinion of the International Searching Authority in connection with International Application No. PCT/AU2014/00101, United States Patent Office, dated Feb. 10, 2014.

(Continued)

*Primary Examiner* — Sarah Pihonak
(74) *Attorney, Agent, or Firm* — Marshall, Gerstein & Borun LLP

(57) ABSTRACT

The invention is a method and composition for treating a topical microbial infection in a subject. The method includes the step of administering a therapeutically effective amount of a polyether ionophore, or a therapeutically acceptable salt thereof, to the subject.

12 Claims, 27 Drawing Sheets

(56) References Cited

OTHER PUBLICATIONS

Kugelberg et al., Establishment of a superficial skin infection model in mice by using *Staphylococcus aureus* and *Streptococcus pyogenes. Antimicrob. Agents Chemother.* 49(8): 3435-41 (2005).
Liu, Microbial aspects of polyethers antibiotics: Activity, production, and biosynthesis. *Polyether Antibiotics Naturally Occurring Acid Ionophores vol. 1: Biology*. J.W. Westley, New York. Marcel Dekker Inc. 43-102 (1982).
McRipley et al., Characterization and quantification of experimental surgical-wound infections used to evaluate topical antibacterial agents. *Antimicrob. Agents Chemother.* 10(1): 38-44 (1976).
Naujokat et al., Salinomycin as a drug for targeting human cancer stem cells. *J. Biomed. Biotechnol.* 2012: 950658 (2012).
Stieritz et al., A burned mouse model to evaluate anti-pseudomonas activity of topical agents. *J. Antimicrob. Chemother.* 9(2): 133-40 (1982).

\* cited by examiner

| Strain ID # | Source | Species | Resistance Profile |
|---|---|---|---|
| ATCC 49775 | Human | *S. aureus* | |
| MSS 1 | Cow | *S. aureus* | |
| MSS 2 | Cat | *S. intermedius* | P |
| MSS 3 | Cat | *S. aureus* | P |
| MSS 4 | Unknown | *S. pseudintermedius* | |
| MSS 5 | Dog | *S. intermedius* | |
| MSS 6 | Human | *S. pseudintermedius* | |
| MSS 7 | Dog | *S. pseudintermedius* | P |
| MSS 8 | Dog | *Coagulase negative* | P, Te |
| MSS 9 | Dog | *S. intermedius* | |
| MSS 10 | Dog | *S. intermedius* | |
| MSS 11 | Unknown | *Coagulase negative* | P, Te |
| MSS 12 | Dog | *S. pseudintermedius* | P |
| MSS 13 | Bird | *Coagulase negative* | P, Te |
| MSS 14 | Dog | *S. intermedius* | P |
| MSS 15 | Dog | *S. intermedius* | P, Te |
| MSS 16 | Pig | *Coagulase negative* | P |
| MSS 17 | Pig | *S. aureus* | Cl, E |
| MSS 18 | Dog | *S. intermedius* | P |
| MSS 19 | Dog | *Coagulase negative* | E |
| MSS 20 | Dog | *S. pseudintermedius* | Cl, P, Te |
| MRSA 1 | Human | *S. aureus* | Enr, E, Gn, O, P |
| MRSA 2 | Human | *S. aureus* | Gn, O, P, Tm |
| MRSA 3 | Human | *S. aureus* | E, Enr, O, P |
| MRSA 4 | Human | *S. aureus* | E, Enr, O, P |
| MRSA 5 | Human | *S. aureus* | E, Enr, Gn, O, P, Te |
| MRSA 6 | Human | *S. aureus* | E, Enr, O, P, Tm |
| MRSA 7 | Human | *S. aureus* | E, Enr, Gn, O, P, Tm |
| MRSA 8 | Human | *S. aureus* | E, Gn, O, P, Te, Tm |
| MRSA 9 | Human | *S. aureus* | E, O, P |
| MRSA 10 | Human | *S. aureus* | E, Enr, O, P |
| MRSA 11 | Human | *S. aureus* | O, P |
| MRSA 12 | Human | *S. aureus* | E, O, P, Te |
| MRSA 13 | Human | *S. aureus* | E, O, P |
| MRSA 14 | Human | *S. aureus* | E, O, P |
| MRSA 15 | Human | *S. aureus* | E, O, P |
| MRSA 16 | Human | *S. aureus* | O, P, Te |

FIGURE 1A

| Strain ID # | Source | Species | Resistance Profile |
|---|---|---|---|
| MRSA 17 | Human | S. aureus | E, Enr, Gn, O, P, Tm |
| MRSA 18 | Human | S. aureus | O, P, Tm |
| MRSA 19 | Human | S. aureus | E, O, P, Te, Tm |
| MRSA 20 | Human | S. aureus | Enr, O, P |
| MR-CNS 1 | Dog | Coagulase negative | Enr, Gn, O, P, Tm |

Cl=clindamycin, Enr=enrofloxacin, E=erythromycin, Gn=gentamicin, O=oxacillin, P=penicillin G, Te=tetracycline, Tm=trimethoprim-sulfamethoxazole

FIGURE 1B

| Compound | Ampicillin | LP 1088 | LP 1369 | LP 4525 | LP 6315 | LP 9666 |
|---|---|---|---|---|---|---|
| $MIC_{50}$ | 0.5 | 1 | 1 | 0.5 | 2 | 8 |
| $MIC_{90}$ | 16 | 2 | 2 | 1 | 4 | 64 |
| MIC Range | 0.25 – 32 | 0.5 – 4 | 0.5 – 2 | 0.25 – 1 | 2 – 8 | 2 – >128 |

Figure 5

| Compound | Ampicillin | LP 1088 | LP 1369 | LP 4525 | LP 6315 | LP 9666 |
|---|---|---|---|---|---|---|
| $MIC_{50}$ | 128 | 1 | 1 | 0.5 | 4 | 32 |
| $MIC_{90}$ | >128 | 2 | 1 | 0.5 | 4 | 64 |
| MIC Range | 8 – >128 | 1 – 2 | 0.5 – 2 | 0.25 – 1 | 2 – 16 | 4 – 128 |

Figure 6

| Compound | LP 1088 | LP 1369 | LP 4525 | LP 6315 | LP 9666 |
|---|---|---|---|---|---|
| MBC$_{50}$ | >128 | 64 | >128 | >128 | >128 |
| MBC$_{90}$ | >128 | >128 | >128 | >128 | >128 |
| MBC Range | 4 – >128 | 4 – >128 | 64 – >128 | 64 – >128 | 128 – >128 |

| Compound | LP 1088 | LP 1369 | LP 4525 | LP 6315 | LP 9666 |
|---|---|---|---|---|---|
| $MBC_{50}$ | >128 | >128 | >128 | 128 | >128 |
| $MBC_{90}$ | >128 | >128 | >128 | >128 | >128 |
| MBC Range | 128 – >128 | 64 – >128 | 4 – >128 | 4 – >128 | 128 – >128 |

|  | Growth Control | Ampicillin 1xMIC | Ampicillin 4xMIC | LP 1369 1xMIC | LP 1369 4xMIC | LP 1369 8xMIC |
|---|---|---|---|---|---|---|
| ATCC 49775 | 3.23 | -6.4 | -6.4 | -1.94 | -2.18 | -2.16 |
| MRSA 9 | 4.11 | -6.41 | N/A | -0.84 | -2.82 | -2.52 |

|  | Growth Control | Ampicillin 1xMIC | Ampicillin 4xMIC | LP 6315 1xMIC | LP 6315 4xMIC | LP 6315 8xMIC |
|---|---|---|---|---|---|---|
| ATCC 49775 | 3.23 | -6.4 | -6.4 | -1.49 | -2.47 | -2.42 |
| MRSA 9 | 4.11 | -6.41 | N/A | -0.64 | -3.13 | -2.86 |

| Adelaide # | GLY | SITE OF ISOLATION | Species | BREED | MRSP / MSSP | mec gene Pert | mecA by RT-PCR Adl | Cefoxitin ZD (mm) | Cefoxitin ZD, Adl (mm) | oxacillin ZD (mm) | oxacillin ZD,Adl (mm) | oxacillin Etest MIC (mg/L) |
|---|---|---|---|---|---|---|---|---|---|---|---|---|
| S1P1 | 191 | AXILLA | S. pseudintermedius | | MRSP | POS | POS | 0 | 0 | 0 | 0 | >256 |
| S2P2 | 193 | TISSUE | S. pseudintermedius | Shar pei X | MRSP | POS | POS | 21 | 21 | 0 | 0 | >256 |
| S3P3 | 194 | SKIN SWAB | S. pseudintermedius | Mastiff X | MRSP | POS | POS | 21 | 24 | 0 | 0 | >256 |
| S4P4 | 214 | SKIN SWAB | S. pseudintermedius | CKCS | MRSP | POS | POS | 29 | 20 | 0 | 0 | 2 |
| S5P5 | 215 | SKIN SWAB | S. pseudintermedius | Shar pei | MRSP | POS | POS | 26 | 30 | 0 | 0 | 4 |
| S6P6 | 218 | PAW SWAB | S. pseudintermedius | Dachshund | MRSP | POS | POS | 22 | 26 | 0 | 0 | >256 |
| S7P7 | 219 | SKIN SWAB | S. pseudintermedius | British Bulldog | MRSP | POS | POS | 21 | 19 | 0 | 0 | >256 |
| S8P8 | 220 | SKIN SWAB | S. pseudintermedius | British Bulldog | MRSP | POS | POS | 21 | 22 | 0 | 0 | >256 |
| S9P9 | 96 | SKIN SWAB | S. pseudintermedius | Akita | MRSP | POS | POS | 23 | 26 | 0 | 0 | 4 |
| S10P10 | 190 | SKIN SWAB | S. pseudintermedius | Akita | MRSP | POS | POS | 21 | 25 | 0 | 0 | >256 |
| S11P11 | 187 | TISSUE | S. pseudintermedius | Bull terrier | MSSP | POS | POS | 22 | 21 | 0 | 0 | >256 |
| S12P12 | 188 | SKIN SWAB | S. pseudintermedius | Great Dane | MRSP | POS | POS | 24 | 24 | 0 | 16 | 1.5 |
| S13P13 | 189 | R EAR SWAB | S. pseudintermedius | CKCS | MSSP | NEG | NEG | 36 | 40 | 13 | 36 | 0.125 |
| S14P14 | 185 | TISSUE | S. pseudintermedius | Labrador Retriever | MSSP | NEG | NEG | 34 | 32 | 26 | 29 | 0.25 |
| S15P15 | 191 | TISSUE | S. pseudintermedius | Maltese X | MSSP | NEG | NEG | 33 | 34 | 22 | 25 | 0.25 |
| S16P16 | 194 | SKIN SWAB | S. pseudintermedius | Maltese | MSSP | NEG | NEG | 38 | 42 | 22 | 34 | 0.19 |
| S17P17 | 195 | SKIN SWAB | S. pseudintermedius | Shar pei X | MSSP | NEG | NEG | 36 | 38 | 22 | 26 | 0.25 |
| S18P18 | 196 | TISSUE | S. pseudintermedius | JRT | MSSP | NEG | NEG | 25 | 40 | 22 | 30 | 0.25 |
| S19P19 | 197 | SKIN SWAB | S. pseudintermedius | Labrador Retriever | MSSP | NEG | NEG | 36 | 38 | 25 | 32 | 0.25 |
| S20P20 | 198 | SKIN SWAB | S. pseudintermedius | Fox Terrier | MSSP | NEG | NEG | 38 | 36 | 23 | 30 | 0.25 |
| S21P21 | 199 | R EAR SWAB | S. pseudintermedius | Labrador Retriever | MSSP | NEG | NEG | 36 | 40 | 27 | 37 | 0.125 |
| S22P22 | 200 | SKIN SWAB | S. pseudintermedius | Maltese | MSSP | NEG | NEG | 34 | 35 | 21 | 26 | 0.25 |
| S23P23 | 203 | | | | | | POS | 29 | 26 | 13 | 14 | 1.5 |

Figure 21

|  | mecA by RT-PCR | Penicillin | Ampicillin | Amoxicillin | Erythromicin | Gentamycin | Clindamycin | Ciprofloxacin |
|---|---|---|---|---|---|---|---|---|
| S1P1 | POS | R | R | R | R | R | S | R |
| S2P2 | POS | R | R | R | R | R | I | R |
| S3P3 | POS | R | R | R | R | R | R | R |
| S4P4 | POS | R | R | R | R | R | R | R |
| S5P5 | POS | R | R | R | R | R | R | R |
| S6P6 | POS | R | R | R | R | R | R | R |
| S7P7 | POS | R | R | S | R | R | R | R |
| S8P8 | POS | R | R | R | R | R | R | R |
| S9P9 | POS | R | R | R | R | R | R | R |
| S10P10 | POS | R | R | R | R | S | R | S |
| S11P11 | POS | R | R | S | R | R | I | R |
| S12P12 | POS | R | R | S | S | S | S | S |
| S13P13 | NEG | R | R | S | S | S | S | S |
| S14P14 | NEG | R | R | S | S | S | S | S |
| S15P15 | NEG | R | R | S | S | S | S | S |
| S16P16 | NEG | R | R | S | S | S | S | S |
| S17P17 | NEG | R | R | S | S | S | S | S |
| S18P18 | NEG | R | R | S | S | S | S | S |
| S19P19 | NEG | R | R | S | S | S | S | S |
| S20P20 | NEG | S | S | S | S | S | S | S |
| S21P21 | NEG | R | R | S | S | S | S | S |
| S22P22 | NEG | R | R | S | R | S | S | S |
| S23P23 | POS | R | R | S | R | S | I | S |

FIGURE 22A

| | mecA by RT-PCR | Cephalothin | Chloramphenicol | Tetracycline | Oxytetracycline | Vancomycin | Cefotetan | Moxifloxacin | Rifampin |
|---|---|---|---|---|---|---|---|---|---|
| S1P1 | POS | R | S | R | R | R | S | S | S |
| S2P2 | POS | S | R | S | S | R | S | I | S |
| S3P3 | POS | S | R | I | R | S | R | S | S |
| S4P4 | POS | I | R | R | R | S | S | S | S |
| S5P5 | POS | S | R | R | R | R | S | S | S |
| S6P6 | POS | R | R | I | R | S | S | S | S |
| S7P7 | POS | I | R | R | R | S | S | S | S |
| S8P8 | POS | S | R | R | I | S | S | S | S |
| S9P9 | POS | S | S | I | R | S | S | S | S |
| S10P10 | POS | S | S | R | S | S | S | S | S |
| S11P11 | POS | S | S | S | R | S | S | S | S |
| S12P12 | POS | S | S | S | S | S | S | S | S |
| S13P13 | NEG | S | S | I | I | S | S | S | S |
| S14P14 | NEG | S | S | S | S | S | S | S | S |
| S15P15 | NEG | S | S | S | I | S | S | S | S |
| S16P16 | NEG | S | S | S | S | S | S | S | S |
| S17P17 | NEG | S | S | S | S | S | S | S | S |
| S18P18 | NEG | S | S | R | I | S | S | S | S |
| S19P19 | NEG | S | S | S | S | S | S | S | S |
| S20P20 | NEG | S | S | S | S | S | S | S | S |
| S21P21 | NEG | S | S | S | S | S | S | S | S |
| S22P22 | NEG | S | S | S | S | S | S | S | S |
| S23P23 | POS | S | S | S | S | S | S | S | S |

FIGURE 22B

|  | Column1 | AMP | LP 1369 | LP 4525 | LP6315 |
|---|---|---|---|---|---|
| 1 | S1P1 | 128 | 1 | 0.5 | 2 |
| 2 | S2P2 | 128 | 0.5 | 0.25 | 1 |
| 3 | S3P3 | 128 | 0.5 | 0.5 | 2 |
| 4 | S4P4 | 128 | 0.5 | 0.25 | 1 |
| 5 | S5P5 | 16 | 0.5 | 0.1 | 1 |
| 6 | S6P6 | 64 | 0.5 | 0.25 | 1 |
| 7 | S7P7 | 128 | 0.5 | 0.25 | 1 |
| 8 | S8P8 | 128 | 0.5 | 0.25 | 1 |
| 9 | S9P9 | 32 | 0.5 | 0.25 | 1 |
| 10 | S10P10 | 64 | 1 | 0.25 | 1 |
| 11 | S11P11 | 128 | 0.5 | 0.25 | 1 |
| 12 | S12P12 | 32 | 0.5 | 0.25 | 1 |
| 13 | S13P13 | 0.25 | 0.5 | 0.1 | 1 |
| 14 | S14P14 | 1 | 1 | 0.25 | 2 |
| 15 | S15P15 | 4 | 0.5 | 0.25 | 1 |
| 16 | S16P16 | 0.25 | 0.5 | 0.25 | 1 |
| 17 | S17P17 | 1 | 0.25 | 0.1 | 1 |
| 18 | S18P18 | 4 | 0.25 | 0.25 | 1 |
| 19 | S19P19 | 0.5 | 0.5 | 0.25 | 1 |
| 20 | S20P20 | 4 | 0.5 | 0.25 | 1 |
| 21 | S21P21 | 0.1 | 0.5 | 0.25 | 2 |
| 22 | S22P22 | 8 | 0.5 | 0.25 | 2 |
| 23 | S23P23 | 32 | 0.5 | 0.25 | 1 |

| Column1 | AMP | LP 1369 | LP 4525 | LP6315 |
|---|---|---|---|---|
| MIC50 (µg/ml) | 32 | 0.5 | 0.25 | 1 |
| MIC90 (µg/ml) | 128 | 1 | 0.25 | 2 |
| MIC mode (µg/ml) | 128 | 0.5 | 0.25 | 1 |
| MIC range (µg/ml) | 0.1-128 | 0.25-1 | 0.1-0.25 | 1-2 |

Figure 23

| | MIC | | | MBC | | |
|---|---|---|---|---|---|---|
| Compound | MIC$_{50}$ | MIC$_{90}$ | MIC Range | MBC$_{50}$ | MBC$_{90}$ | MBC Range |
| LP1088 | 1 | 2 | 0.25-4 | 128 | x | 4-x |
| LP1369 | 2 | 4 | 0.5-8 | 64 | x | 2-x |
| LP4525 | 0.25 | 1 | 0.25-2 | 128 | x | 2-x |
| LP6315 | 0.5 | 4 | 0.25-8 | 128 | x | 4-x |
| LP9666 | 32 | 128 | 1-x | x | x | 64-x |
| Ampicillin | 0.25 | 0.25 | 0.25-0.5 | N/A | N/A | N/A |

Note: 'x' indicates confluent growth

| | MIC | | | MBC | | |
|---|---|---|---|---|---|---|
| Compound | MIC$_{50}$ | MIC$_{90}$ | MIC Range | MBC$_{50}$ | MBC$_{90}$ | MBC Range |
| LP1088 | 1 | 2 | 1-4 | x | x | 4-x |
| LP1369 | 1 | 4 | 0.5-8 | x | x | 2-x |
| LP4525 | 0.5 | 1 | 0.25-1 | 64 | x | 2-x |
| LP6315 | 4 | 4 | 1-4 | 128 | x | 4-x |
| LP9666 | 32 | 128 | 8-128 | x | x | 64-x |
| Ampicillin | 0.25 | 0.5 | 0.25-0.5 | N/A | N/A | N/A |

Note: 'x' indicates confluent growth

| Compound | MIC | | | MBC |
|---|---|---|---|---|
| | MIC$_{50}$ | MIC$_{90}$ | MIC Range | Range |
| LP1088 | 2 | 4 | 0.5-4 | 4-x |
| LP1369 | 2 | 8 | 0.5-8 | 32-x |
| LP4525 | 0.5 | 1 | 0.25-1 | 8-x |
| LP6315 | 2 | 8 | 0.25-8 | 32-x |
| LP9666 | 64 | 128 | 4-128 | x |
| Ampicillin | 0.25 | 0.25 | - | N/A |

Note: 'x' indicates confluent growth

Figure 27

| Compound | MIC | | | MBC | | |
|---|---|---|---|---|---|---|
| | MIC$_{50}$ | MIC$_{90}$ | MIC Range | MBC$_{50}$ | MBC$_{90}$ | MBC Range |
| LP1088 | 0.5 | 1 | 0.25-2 | x | x | 64-x |
| LP1369 | 2 | 4 | 2-4 | x | x | 64-x |
| LP4525 | 0.25 | 0.25 | 0.25-2 | 64 | 128 | 16-x |
| LP6315 | 0.25 | 0.5 | 0.25-0.5 | 128 | 128 | 8-x |
| LP9666 | 32 | 64 | 4-128 | x | x | x |
| Ampicillin | 0.25 | 0.25 | - | N/A | N/A | N/A |

Note: 'x' indicates confluent growth

Figure 28

| Compound | MIC | | | MBC |
|---|---|---|---|---|
| | MIC$_{50}$ | MIC$_{90}$ | MIC Range | Range |
| LP1088 | 1 | 1 | 0.25-1 | 8-x |
| LP1369 | 2 | 4 | 0.5-4 | 32-128 |
| LP4525 | 0.25 | 0.25 | - | 4-x |
| LP6315 | 0.25 | 0.25 | - | 4-128 |
| LP9666 | 4 | 32 | 1-32 | x |
| Ampicillin | 0.5 | 0.5 | 0.25-0.5 | N/A |

Note: 'x' indicates confluent growth

Figure 29

| Farm | Cow | Quarter | Gram strain | Catalase test | Coagulase | Esculin | CAMP | Level of Haemolysis | Lancefield Group |
|---|---|---|---|---|---|---|---|---|---|
| MAM | 865 | LR | Positive | Positive | Positive | - | - | γ-haemolytic | - |
| MAM | 940 | RR | Positive | Negative | - | Negative | Negative | γ-haemolytic | Ungrouped |
| MAM | 954 | RR2 | Positive | Positive | Negative | - | - | γ-haemolytic | - |
| MAM | 954 | RR1 | Positive | Positive | Positive | - | - | β-haemolytic | - |
| BEV | 978 | RR1 | Positive | Positive | Negative | - | - | α-haemolytic | - |
| MAM | 1041 | RF1 | Positive | Positive | Positive | - | - | β-haemolytic | - |
| MAM | 1041 | RF2 | Positive | Positive | Positive | - | - | β-haemolytic | - |
| MAM | 1051 | RF1 | Positive | Positive | Positive | - | - | γ-haemolytic | - |
| MAM | 1060 | LR | Positive | Positive | Negative | - | - | γ-haemolytic | - |
| MAM | 1092 | LR | Positive | Positive | Positive | - | - | β-haemolytic | - |
| MAM | 1096 | RF | Positive | Positive | Positive | - | - | β-haemolytic | - |
| MAM | 1155 | LR | Positive | Positive | Positive | - | - | γ-haemolytic | - |
| MAM | 1155 | LF | Positive | Positive | Negative | - | - | γ-haemolytic | - |
| MAM | 1194 | LF | Positive | Positive | Positive | - | - | γ-haemolytic | - |
| MAM | 1196 | LF | Positive | Positive | Negative | Negative | - | β-haemolytic | - |
| MAM | 1222 | RF | Positive | Positive | Positive | - | - | γ-haemolytic | - |
| MAM | 1232 | LF | Positive | Positive | Positive | - | - |  | - |
| MAM | 1232 | LR | Positive | Positive | Positive | - | - | β-haemolytic | - |
| MAM | 1251 | RF | Negative | Negative | - | - | Negative | α-haemolytic | - |
| MAM | 1271 | RF1 | Positive | Positive | Negative | - | - | γ-haemolytic | - |
| MAM | 1271 | RF | Positive | Positive | Negative | - | - | γ-haemolytic | - |
| MAM | 1271 | RF2 | Positive | Negative | - | - | Negative | α-haemolytic | Ungrouped |
| MAM | 1283 | LF2 | Positive | Positive | - | Positive | - | γ-haemolytic | - |
| MAM | 1283 | LF1 | Positive | Positive | - | - | - | α-haemolytic | - |
| BEV | 1304 | RR | Positive | Negative | - | Negative | Negative | β-haemolytic | B |
| BEV | 1337 | FR2 | Positive | Negative | - | Negative | Negative | β-haemolytic | B |
| BEV | 1337 | FL | Positive | Positive | - | Positive | Negative | α-haemolytic | Ungrouped |
| BEV | 1337 | FR1 | Positive | Negative | - | Negative | Negative | β-haemolytic | B |
| BEV | 1346 | FR | Positive | Negative | - | Negative | Negative | β-haemolytic | B |
| BEV | 1346 | RR1 | Positive | Negative | - | Negative | Negative | β-haemolytic | B |

FIGURE 30A

| Farm | Cow | Quarter | Gram strain | Catalase test | Coagulase | Esculin | CAMP | Level of Haemolysis | Lancefield Group |
|---|---|---|---|---|---|---|---|---|---|
| BEV | 1346 | RR | Positive | Negative | - | Negative | Negative | - | B |
| BEV | 1346 | FL | Positive | Negative | - | Negative | Negative | β-haemolytic | B |
| BEV | 1346 | RL | Positive | Negative | - | Negative | Negative | β-haemolytic | B |
| BEV | 1537 | FL | Positive | Positive | Positive | - | - | γ-haemolytic | - |
| BEV | 1591 | RF1 | Positive | Negative | - | - | - | α-haemolytic | Ungrouped |
| BEV | 1765 | RR | Positive | Positive | Negative | - | - | α-haemolytic | - |
| BEV | 1765 | RR1 | Positive | Negative | - | Negative | Negative | β-haemolytic | B |
| BEV | 2448 | RL | Negative | Positive | - | - | - | - | - |
| BEV | 2530 | FLW | Positive | Positive | Negative | - | - | γ-haemolytic | - |
| BEV | 2825 | FR | Negative | Positive | - | - | - | - | - |
| BEV | 2825 | RR | Negative | Negative | Negative | - | - | γ-haemolytic | - |
| BEV | 3071 | RL2 | Positive | Negative | - | Negative | Negative | β-haemolytic | B |
| BEV | 3078 | RRL2 | Positive | Negative | - | Negative | Negative | β-haemolytic | B |
| BEV | 3179 | RL | Positive | Negative | - | Negative | Negative | β-haemolytic | B |
| BEV | 3956 | RL | Positive | Negative | - | - | Negative | β-haemolytic | B |
| BEV | 4027 | RR | Positive | Positive | Negative | - | - | γ-haemolytic | - |
| BEV | 6019 | FR1 | Positive | Negative | - | Negative | Negative | α-haemolytic | Ungrouped |
| BEV | 6121 | FL | Positive | Positive | Negative | - | - | γ-haemolytic | - |
| BEV | 6154 | RL | Positive | Negative | - | Negative | Negative | α-haemolytic | Ungrouped |
| BEV | 6175 | FL | Positive | Negative | - | Positive | Negative | α-haemolytic | Ungrouped |
| CTRL | 6533 | Control strain | Positive | Positive | Positive | - | - | - | - |

FIGURE 30B

| Farm | Cow | Quarter | Cellular morphology | Additional morphology comments | Size of singe cells | Diagnosis |
|---|---|---|---|---|---|---|
| MAM | 865 | LR | Cocci | Very round | Medium | S. aureus |
| MAM | 940 | RR | Cocci | Lancet shaped | Small | S. uberis |
| MAM | 954 | RR2 | Cocci | Round, clustered | Medium | Coagulase negative Staph |
| MAM | 954 | RR1 | Cocci | Round, clustered | Medium | S. aureus |
| BEV | 978 | RR1 | Rod | Chains | Large | Bacillus spp. |
| MAM | 1041 | RF1 | Cocci | Clustered | Medium | S. aureus |
| MAM | 1041 | RF2 | Cocci | Round | Medium | S. aureus |
| MAM | 1051 | RF1 | Cocci | Round | Medium | S. aureus |
| MAM | 1060 | LR | Cocci | Round, clustered | Medium | Coagulase negative Staph |
| MAM | 1092 | LR | Cocci |  | Small | S. aureus |
| MAM | 1096 | RF | Cocci | Small noticeable filaments protruding from each cluster | Medium | S. aureus |
| MAM | 1155 | LR | Cocci | Very round | Medium | S. aureus |
| MAM | 1155 | LF | Cocci | Grape-like | Medium | S. aureus |
| MAM | 1194 | LF | Cocci | Small, round | Medium | Coagulase negative Staph |
| MAM | 1196 | LF | Cocci | Grape-like | Small | S. aureus |
| MAM | 1222 | RF | Cocci |  | Small | Coagulase negative Staph |
| MAM | 1232 | LF | Cocci |  | Small | S. uberis |
| MAM | 1232 | LR | Cocci | Round, clustered | Medium | S. aureus |
| MAM | 1251 | RF | Cocci | Lancet shaped | Medium | S. aureus |
| MAM | 1271 | RF1 | Cocci | Round, grape-like | Small | Unidentified Gm negative |
| MAM | 1271 | RF | Cocci | Small, round | Small | Coagulase negative Staph |
| MAM | 1271 | RF2 | Cocci | Highly clustered cocci | Small | Coagulase negative Staph |
| MAM | 1283 | LF2 | Cocci | Very small | Small | S. uberis |
| MAM | 1283 | LF1 | Cocci | Grape-like, clustered | Medium | S. aureus |
| BEV | 1304 | RR | Rod | Very small, oval/rod shaped, arranged in a palisade | Small | S. aureus |
| BEV | 1337 | FR2 | Cocci | Very round | Medium | S. agalactiae |
| BEV | 1337 | FL | Cocci |  | Small | S. agalactiae |
| BEV | 1337 | FR1 | Cocci | Round | Medium | S. uberis |

FIGURE 30C

| Farm | Cow | Quarter | Cellular morphology | Additional morphology comments | Size of singe cells | Diagnosis |
|---|---|---|---|---|---|---|
| BEV | 1346 | FR | Cocci | Lancet shaped | Small | S. agalactiae |
| BEV | 1346 | RR1 | Cocci | Lancet shaped | Medium | S. agalactiae |
| BEV | 1346 | RR | Cocci | Lancet shaped | Small | S. agalactiae |
| BEV | 1346 | FL | Cocci | Lancet shaped | Small | S. agalactiae |
| BEV | 1346 | RL | Cocci | Round | Small | S. agalactiae |
| BEV | 1537 | FL | Flat diplococci | Lancet shaped, very clustered | Medium | S. aureus |
| BEV | 1591 | RF1 | Cocci | Lancet shaped | Small | S. uberis |
| BEV | 1765 | RR | Cocci | small, round | Small | Coagulase negative Staph |
| BEV | 1765 | RR1 | Cocci | | | S. agalactiae |
| BEV | 2448 | RL | Cocci | Short, fat rod | Small | Unidentified Gm negative |
| BEV | 2530 | FLW | Cocci | | | Coagulase negative Staph |
| BEV | 2825 | FR | Cocci | Lancet shaped | Small | Unidentified Gm negative |
| BEV | 2825 | RR | Cocci | Lancet shaped | Small | Unidentified Gm negative |
| BEV | 3071 | RL2 | Cocci | | | S. agalactiae |
| BEV | 3078 | RRL2 | Cocci | Lancet shaped | Medium | S. agalactiae |
| BEV | 3179 | RL | Cocci | Lancet shaped | Small | S. agalactiae |
| BEV | 3956 | RL | Cocci | Lancet shaped | Small | S. agalactiae |
| BEV | 4027 | RR | Hypae and buds | Coccus irregular shape | | Unidentified yeast |
| BEV | 6019 | FR1 | Cocci | Lancet shaped | Medium | S. uberis |
| BEV | 6121 | FL | Cocci | | | Coagulase negative Staph |
| BEV | 6154 | RL | Cocci | Lancet shaped | Small | S. uberis |
| BEV | 6175 | FL | Cocci | Very small, round | Small | S. uberis |
| CTRL | 6533 | Control strain | Cocci | Round, grape-like | Large | S. aureus |

FIGURE 30D

| MIC | | Compound | | | | | |
| --- | --- | --- | --- | --- | --- | --- | --- |
| Cow | Quarter | Amp | LP1088 | LP1369 | LP4525 | LP6315 | LP9666 |
| 865 | LR | | | | | | |
| 940 | RR | | | | | | |
| 954 | RR1 | 0.25 | 2 | 1 | 0.5 | 2 | 64 |
| 954 | RR2 | 0.25 | 2 | 1 | 0.5 | 4 | x |
| 978 | RR1 | | | | | | |
| 1041 | RF1 | 0.5 | 2 | 1 | 0.5 | 4 | 128 |
| 1041 | RF2 | 0.25 | 1 | 0.5 | 0.25 | 2 | 32 |
| 1051 | RF1 | 0.25 | 2 | 1 | 0.5 | 4 | 16 |
| 1060 | LR | | | | | | |
| 1092 | LR | 0.25 | 1 | 0.5 | 0.5 | 4 | 16 |
| 1096 | RF | 0.25 | 1 | 0.5 | 0.25 | 4 | 16 |
| 1155 | LF | 0.25 | 1 | 0.5 | 0.25 | 4 | 64 |
| 1155 | LR | 0.25 | 4 | 4 | 1 | 1 | 32 |
| 1194 | LF | 0.25 | 4 | 8 | 1 | 2 | x |
| 1196 | LF | 0.25 | 1 | 1 | 0.25 | 4 | 64 |
| 1222 | RF | 0.25 | 0.5 | 2 | 0.25 | 0.25 | 16 |
| 1232 | LF | 0.5 | 1 | 1 | 0.5 | 2 | 128 |
| 1232 | LR | 0.25 | 1 | 0.5 | 0.25 | 2 | 8 |
| 1251 | RF | 0.25 | 1 | 1 | 0.5 | 2 | 64 |
| 1271 | RF1 | | 0.5 | 1 | 0.25 | 0.25 | 8 |
| 1271 | RF | | | | | | |
| 1271 | RF2 | | | | | | |
| 1283 | LF2 | 0.5 | 1 | 1 | 0.25 | 0.25 | 1 |
| 1283 | LF1 | | 0.25 | 0.5 | 0.25 | 0.25 | 2 |
| 1337 | FR1 | | 0.25 | 0.5 | 0.25 | 0.25 | 16 |
| 1337 | FR2 | 0.25 | 2 | 2 | 0.25 | 0.25 | 4 |
| 1337 | FL | | 1 | 4 | 0.25 | 0.5 | 32 |
| 1346 | FR | | 0.5 | 4 | 0.25 | 0.25 | 128 |
| 1346 | RR1 | | 0.5 | 2 | 0.25 | 0.25 | 16 |
| 1346 | RR | | 0.25 | 2 | 2 | 0.25 | 4 |
| 1346 | FL | | 1 | 2 | 0.25 | 0.25 | 16 |
| 1346 | RL | | 0.5 | 2 | 0.25 | 0.25 | 32 |
| 1537 | FL | 0.5 | 2 | 4 | 0.5 | 0.25 | 16 |
| 1591 | RF1 | | | | | | |
| 1765 | RR | 0.25 | 2 | 4 | 0.25 | 0.25 | 4 |
| 1765 | RR1 | | 1 | 4 | 0.25 | 0.5 | 64 |
| 2530 | FLW | 4 | x | x | x | x | x |
| 3071 | RL2 | | 0.5 | 2 | 0.25 | 0.25 | 16 |
| 3078 | RRL2 | | 0.5 | 2 | 0.25 | 0.5 | 32 |
| 3179 | RL | | 1 | 2 | 0.25 | 0.25 | 32 |
| 3956 | RL | | 0.5 | 2 | 0.25 | 0.25 | 8 |
| 4027 | RR | x | x | x | x | x | x |
| 6019 | FR1 | | 0.25 | 1 | 0.25 | 0.25 | 2 |
| 6121 | FL | 0.25 | 2 | 0.5 | 0.25 | 1 | 128 |
| 6154 | RL | | 0.5 | 2 | 0.25 | 0.25 | 32 |
| 6175 | FL | 0.5 | 1 | 2 | 0.25 | 0.25 | 2 |
| 1304 | RR | | | | | | |
| 1591 | RR | | | | | | |
| 6533 | S. aureus control strain | 0.25 | 1 | 1 | 0.25 | 2 | 8 |

Note: 'x' indicates confluent growth.

Figure 31

| MBC | | Compound | | | | |
|---|---|---|---|---|---|---|
| Cow | Quarter | LP1088 | LP1369 | LP4525 | LP6315 | LP9666 |
| 865 | LR | | | | | |
| 940 | RR | | | | | |
| 954 | RR1 | 128 | x | x | 128 | x |
| 954 | RR2 | x | x | 128 | x | x |
| 978 | RR1 | 64 | 16 | 32 | 128 | 128 |
| 1041 | RF1 | 128 | x | 64 | 128 | x |
| 1041 | RF2 | 8 | x | 8 | 64 | 64 |
| 1051 | RF1 | x | x | x | x | x |
| 1060 | LR | 4 | x | 128 | 32 | x |
| 1092 | LR | x | x | 128 | x | x |
| 1096 | RF | x | x | 128 | 128 | x |
| 1155 | LF | 128 | 128 | 128 | 128 | x |
| 1155 | LR | x | 64 | 128 | 64 | x |
| 1194 | LF | x | x | 64 | x | x |
| 1196 | LF | x | x | 32 | x | x |
| 1222 | RF | 128 | 32 | 32 | 32 | x |
| 1232 | LF | 64 | 128 | 16 | 32 | x |
| 1232 | LR | 128 | x | 64 | 64 | x |
| 1251 | RF | 4 | 2 | 2 | 4 | x |
| 1271 | RF1 | 64 | 64 | 32 | 8 | x |
| 1271 | RF | 128 | x | 32 | 128 | x |
| 1271 | RF2 | | | | | |
| 1283 | LF2 | 32 | 64 | 8 | 16 | x |
| 1283 | LF1 | 128 | 64 | 64 | 64 | x |
| 1337 | FR1 | x | 128 | x | 64 | x |
| 1337 | FR2 | 64 | 64 | 16 | 16 | x |
| 1337 | FL | x | 128 | 128 | 128 | x |
| 1346 | FR | x | 128 | 64 | 128 | x |
| 1346 | RR1 | 128 | 128 | 64 | 128 | x |
| 1346 | RR | 64 | 64 | 16 | 32 | x |
| 1346 | FL | x | 128 | 128 | 128 | x |
| 1346 | RL | x | 128 | 64 | 128 | x |
| 1537 | FL | 64 | 32 | 32 | 16 | x |
| 1591 | RF1 | | | | | |
| 1765 | RR | 16 | 64 | 8 | 32 | x |
| 1765 | RR1 | 64 | 64 | 32 | 8 | x |
| 2530 | FLW | 128 | x | x | x | x |
| 3071 | RL2 | x | 128 | 128 | 64 | x |
| 3078 | RRL2 | x | 128 | 64 | 128 | x |
| 3179 | RL | x | 128 | 128 | x | x |
| 3956 | RL | x | 128 | 64 | 64 | x |
| 4027 | RR | | x | x | x | x |
| 6019 | FR1 | 128 | 64 | 32 | 32 | x |
| 6121 | FL | 128 | 32 | 64 | 128 | x |
| 6154 | RL | x | 128 | 64 | 128 | x |
| 6175 | FL | 16 | 32 | 4 | 4 | x |
| 1304 | RR | | | | | |
| 1591 | RR | | | | | |
| 6533 | S. aureus control strain | | | | | |

Figure 32

Group Statistics

| | Treatment | N | Mean | Std. Deviation | Std. Error Mean |
|---|---|---|---|---|---|
| logCFU/g | 0 | 5 | 8.98 | .070 | .032 |
| | 1 | 5 | 6.17 | .389 | .174 |

Independent Samples Test

| | | Levene's Test for Equality of Variances | | t-test for Equality of Means | | | | | |
|---|---|---|---|---|---|---|---|---|---|
| | | F | Sig. | t | df | Sig. (2-tailed) | Mean Difference | Std. Error Difference | 95% Confidence Interval of the Difference | |
| | | | | | | | | | Lower | Upper |
| log CFU/g | Equal variances assumed | 6.199 | .038 | 15.897 | 8 | .000 | 2.807 | .177 | 2.490 | 3.215 |
| | Equal variances not assumed | | | 15.897 | 4.263 | .000 | 2.807 | .177 | 2.329 | 3.285 |

FIGURE 34A

METHODS OF TREATING TOPICAL MICROBIAL INFECTIONS

TECHNICAL FIELD

This invention relates to methods of treatment and prevention of microbial skin infection or carriage in a subject, topical pharmaceutical antimicrobial compositions when used therein, and veterinary compositions when used therein.

BACKGROUND ART

Infection in both human and veterinary medicine is often caused by infection with bacteria of the *Staphylococcus* genus. Staphylococci are commensals of healthy mammals and birds and may be found on the skin and in associated glands, the nares, and transiently in the gastrointestinal tract as well as on the mucous membranes of the upper respiratory and lower urogenital tracts. While many strains and species of *Staphylococcus* do not cause disease, certain strains and species are capable of opportunistic pathogenicity. Two major pathogenic species of *Staphylococcus* of medical and veterinary significance are *Staphylococcus aureus* and *Staphylococcus pseudintermedius*. *Staphylococcus aureus* is associated with skin and post-operative wound infections, while *Staphylococcus pseudintermedius* is commonly associated with pyogenic skin and post-operative wound infections in dogs and cats. *Staphylococcus pseudintermedius* has been identified as the main pathogenic species of veterinary significance in the *Staphylococcus pseudintermedius* group (SIG), which includes the strains *Staphylococcus intermedius*, *Staphylococcus pseudintermedius*, and *Staphylococcus delphini*.

Treatment of Bacteria with Antibiotics

The treatment of *Staphylococcus* bacteria can be difficult, particularly when subjects are infected with antibiotic-resistant strains. Bacterial infection by *Staphylococcus* is usually treated by the administration of β-lactam antimicrobials, a class of antimicrobials that target penicillin binding proteins (PBPs) which function in bacterial cell wall biosynthesis. These antimicrobials have bactericidal activity and function by inhibiting biosynthesis of the bacterial cell wall, resulting in high internal osmotic pressure, causing the bacteria to lyse. However, the use, overuse and misuse of antimicrobials in the treatment of bacterial infections has resulted in the emergence of antimicrobial resistant bacteria, to which the *Staphylococcus* genus is particularly prone. Resistance mechanisms in some species of *Staphylococcus* bacteria include the secretion of β-lactamase enzymes capable of hydrolysing the β-lactam ring of β-lactam antimicrobials. To address this form of resistance, β-lactamase inhibitors, such as clavulanic acid are typically co-administered together with β-lactam antimicrobials, or synthetic analogues of penicillin, such as methicillin, that are not substrates of β-lactamase, can be used.

Recently, even combination treatment has proved ineffective against antibiotic resistant strains of *Staphylococcus*. The emergence of methicillin-resistant *Staphylococcus aureus* isolates (MRSA) has effectively prevented the use of methicillin and other β-lactam antimicrobials that are not inactivated by β-lactamases. MRSA isolates have now been found to possess the mecA resistance gene which encodes mutated penicillin binding proteins or PBPs and confers resistance to penicillin, as well as to its analogues, and other β-lactam antimicrobials, including most cephalosporins and carbapenems. The issue of MRSA is often encountered in hospitals where MRSA bacterial isolates have been transferred to patients, as hospital-acquired MRSA (HA-MRSA) which is often maintained within hospitals through the colonisation of hospital equipment and staff. Unfortunately, patients who are immunosuppressed, have wounds or other trauma, are predisposed to easily contract MRSA infections, as well as infections with other species of staphylococci. This has caused many hospitals to implement anti-MRSA measures so as to reduce the incidence of HA-MRSA infections. A more recent concern has been the emergence of MRSA strains outside of hospitals, referred to as community-acquired MRSA (CA-MRSA). These strains are often even more virulent than HA-MRSA strains and may cause necrotising fasciitis.

In addition to MRSA, methicillin-resistance has also been observed in other species of staphylococci. For example, many strains of non-pathogenic, coagulase-negative species of *Staphylococcus* (MR-CNS) and *Staphylococcus pseudintermedius* (MRSP) are known to be methicillin-resistant. Other resistant species include the Gram negative MDR *Pseudomonas aeruginosa*, and MDR *Escherichia coli* and *Enterobacter* species and the Gram positive vancomycin resistant Enterococcci (VRE) and resistant *Streptococcus* spp.

The emergence of resistance to antibiotics has increased the need to provide alternative compounds capable of inhibiting multi-resistant bacterial strains, such as MRSA and MRSP.

Polyether Ionophores

Carboxyl polyethers, also known as polyether antibiotics or polyether ionophores, form electrically neutral complexes with monovalent or divalent cations, catalysing electrically silent exchanges of cations or protons across a variety of biological membranes. These compounds have been reported as showing a high degree of promise for the potential control of drug-resistant bacterial and protozoal infections however their use is severely limited by their high toxicity. These molecules function by rendering cell or intracellular membranes permeable to cations which are normally asymmetrically distributed across biological membranes thereby forming steep concentration gradients. Examples of polyether ionophores include lasalocid, monensin, narasin, salinomycin, semduramicin, maduramicin and laidlomycin.

However, the acute toxicity of these compounds due to their erythrocyte lysing activity and cardiac toxicity has effectively prevented their use in vivo. The main obstacle to the use of polyether ionophores as drugs to control human diseases is the issue of toxicity. In one example, as reported by Naujokat and Steinhart (2012, *J Biomed Biotechnol* 950658), considerable toxicity of salinomycin was reported in humans. In this case, the accidental inhalation and swallowing of about 1 mg/kg salinomycin by a 35-year-old male human, resulted in severe acute and chronic salinomycin toxicity with acute nausea together with photophobia, leg weakness, tachycardia and blood pressure elevation and a chronic (day 2 to day 35) creatine kinase elevation, myoglobinuria, limb weakness, muscle pain, and mild rhabdomyolysis. The European Food Safety Authority has recently published risk assessment data declaring an acceptable daily intake (ADI) of 5 μg/kg salinomycin for humans, since daily intake of more than 500 μg/kg salinomycin by dogs leads to neurotoxic effects, such as myelin loss and axonal degeneration (Naujokat and Steinhart, 2012, supra). In another example, Liu (1982, *Polyether Antibiotics. Naturally Occurring Acid Ionophores*. Volume 1. Biology. J. W. Westley. New York, Marcel Dekker Inc: 43-102) cites the high oral and parenteral toxicity of polyether ionophores is the likely reason why there has been no report on the in vivo antimicrobial activity of polyether ionophores.

The only current applications for polyether ionophores of which the applicant is aware, is their application as orally administered agents in veterinary medicine as controls of coccidiosis and for growth promotion.

Furthermore, not all polyether ionophores have shown significant activity against gram-positive bacteria such as *Staphylococcus aureus* and most do not have broad-spectrum activity against gram-negative bacteria. In view of the considerable toxicity in mammals, as reported by Naujokat and Steinhart (2012 supra), salinomycin has only been used as a coccidistat and growth promoter in livestock, and is not regarded as a suitable candidate for human drug development.

There remains a need for alternative antimicrobials in the treatment of infection by multi-resistant bacteria, such as MRSA and MRSP. However, as reported by the Infectious Diseases Society of America and the European Centre for Disease Control and Prevention, few new drugs are being developed that offer promising results over existing treatments, and even fewer of these are specifically administered for the treatment of staphylococci (Gilbert et al. 2010, *Clinical Infectious Diseases*, 50(8):1081-1083).

The object of the present invention is to overcome some or all of the shortcomings of the prior art.

The discussion of the background art set out above is intended to facilitate an understanding of the present invention only. The discussion is not an acknowledgement or admission that any of the material referred to is or was part of the common general knowledge as at the priority date of the application.

SUMMARY OF INVENTION

According to one aspect of the invention, there is provided a method of treating a microbial infection in a subject, the method including the step of administering a therapeutically effective amount of a polyether ionophore, or a therapeutically acceptable salt thereof, to the subject. Preferably, the microbial infection is a topical microbial infection. Preferably, the ionophore is applied topically. More preferably, the ionophore is applied to the site of infection topically.

According to another aspect of the invention, there is provided a method of preventing a microbial infection in a subject, the method including the step of administering a therapeutically effective amount of a polyether ionophore, or a therapeutically acceptable salt thereof, to the subject. The topical infection may be an infection of the skin, the nasal cavity, external ear canal or eye. Preferably, the microbial infection is a topical microbial infection. Preferably, the ionophore is applied topically. More preferably, the ionophore is applied to the site of infection topically.

According to another aspect of the invention, there is provided the use of a polyether ionophore, or a therapeutically acceptable salt thereof, in the manufacture of medicament for the treatment of a topical microbial infection in a subject.

The administration may be topical administration directly to the skin, nasal cavity, ear canal or eye. As an example, the administration may be via the external ear canal to treat otitis externa or by intranasal deposition to treat carriage of MRSA.

The method may be a method of treating a microbial carriage or infection of the skin and nares of a subject.

The topical administration may comprise the administration of the therapeutically effective amount of polyether ionophore directly to a surface of the subject. Preferably, the ionophore is applied topically to the skin, nares, external ear canal or eye of the subject. The use may comprise administering a therapeutically effective amount of a polyether ionophore, or a therapeutically acceptable salt thereof, to the skin, nares, ear canal or eye of a subject.

Further features of the invention provide for the polyether ionophore, or the therapeutically acceptable salt thereof, to be selected from the group comprising monensin (also known as A-3823A), narasin A (also known as A-28086A), narasin B (also known as A-28086B), narasin D (also known as A-28086D), lasalocid, salinomycin, and maduramicin, alborixin (also known as S-14750A, CP-38,986), laidlomycin (also known as AB-78), lenoremycin (also known as A-130A, Ro21-6150), A-130B, A-130C, dianemycin (also known as A-150 (M5-16183), A-204A, A-204B, lonomycin (also known as A-218), deoxylaidlomycin (also known as A-712), calcimycin (also known as A-23187), septamycin (also known as BL-580α and A-28695A), A-28695B, K-41A (also known as A-32887), septamycin (also known as BL-580α$^b$), BL-580β, BL-580δ, BL-580Z, carriomycin, calmycin$^b$ (also known as A-23187), cationomycin, chloronoboritomycin A (also known as X-14766A), etheromycin (also known as CP-38,295, C 20-12, T-40517), deoxy-salinomycin (also known as SY-1), deoxy-epi-salinomycin (SY-2), deoxy-narasin, deoxy-epi-narasin, dianemycon$^b$ (also known as M5-16183, A-150), emericid (also known as lonomycin A and DE 3938), duamycin (also known as nigericin, helixin C, and azalomycin M), gridorixin, ionomycin, K-41 B, lasalocid A (X-537A), lasalocid B, lasalocid C, lasalocid D, lasalocid E, iso-lasalocid A, leuseramycin, lomomycin B, lomomycin C, lysocellin, M-139603, monensin B, monensin C, monensin D, mutalomycin, noboritomycin A, noboritomycin B, RP 30504, RP 37454, salinomycin, salinomycin AII, SY-4, SY-5, SY-8, tetronomycin, TM-531 B, TM-531C, X-206, X-14547A, X-14667A, X-14667B, X-14868A, X-14868B, X-14868C, X-14868D, 5057, 6016.

Preferably the polyether ionophore is selected from the group comprising salinomycin; lasalocid; narasin; maduramicin; monensin, laidlomycin, and semduramicin.

In one embodiment, the polyether ionophore is not nigericin. In one embodiment, the polyether ionophore is not ionomycin.

The subject may be any subject capable of colonisation by microbes. The subject may be mammalian or avian. Preferably, the subject is selected from the group comprising human, canine, avian, porcine, bovine, ovine, equine, and feline. Most preferably, the subject is selected from the group comprising human, bovine, porcine, equine, feline and canine.

In one embodiment, the polyether ionophore is administered to the subject at a dosage selected from the group comprising 5 µg/g to 900,000 mg/g, preferably 5 µg/g to 500 mg/g, more preferably 5 µg/g to 100 mg/g, most preferably preferably 16 µg/g to 52 mg/g.

In one embodiment of the invention, the polyether ionophore is administered to the subject at a dosage comprising 16 µg/g to 52 mg/g.

In one embodiment, the polyether ionophore is administered to the subject at a dosage selected from the group comprising 1 ug/g to 100 ug/g; 100 ug/g to 200 ug/g; 200 ug/g to 300 ug/g; 300 ug/g to 400 ug/g; 400 ug/g to 500 ug/g; 500 ug/g to 600 ug/g; 600 ug/g to 700 ug/g; 700 ug/g to 800 ug/g; 800 ug/g to 900 ug/g; and 900 ug/g to 1000ug/g. In one embodiment, the polyether ionophore is administered to the subject at a dosage selected from the group comprising 1 ug/g to 10 ug/g; 10 ug/g to 20 ug/g; 20 ug/g to 30 ug/g; 30 ug/g to 40 ug/g; 40 ug/g to 50 ug/g; 50 ug/g to 60 ug/g; 60 ug/g to 70 ug/g; 70 ug/g to 80 ug/g; 80 ug/g to 90 ug/g; and 90 ug/g to 100 ug/g. In one embodiment, the polyether ionophore is administered to the subject at a dosage selected from the group comprising 1 mg/g to 100 mg/g; 100 mg/g to 200 mg/g; 200 mg/g to 300 mg/g; 300 mg/g to 400 mg/g; 400 mg/g to 500 mg/g; 500 mg/g to 600 mg/g; 600 mg/g to 700 mg/g; 700 mg/g to 800 mg/g; 800 mg/g to 900 mg/g; and 900 mg/g to 1000mg/g. In one embodiment, the polyether ionophore is administered to the subject at a dosage selected from the group comprising 1 mg/g to 10 mg/g; 10 mg/g to 20 mg/g; mg/g; 20 mg/g to 30 mg/g; 30 mg/g to 40 mg/g; 40 mg/g to 50 mg/g; 50 mg/g to 60 mg/g; 60 mg/g to 70 mg/g; 70 mg/g to 80 mg/g; 80 mg/g to 90 mg/g; and 90 mg/g to 100 mg/g In one embodiment of the invention, the polyether ionophore is administered to the subject using a dosing regimen selected from the group consisting of: three times daily; two times daily; daily; every second day, every third day, once weekly; once fortnightly and once monthly.

In one embodiment of the invention, the polyether ionophore is administered to the subject at a total dosage quantity per dose selected from the group consisting of: between 1 mg to 1000 mg; between 10 mg and 500 mg; between, 10 mg and 400 mg; between 10 mg and 300 mg; between 10 mg and 200 mg; between 10 mg and 100 mg; and between 50 mg and 100 mg. In one embodiment of the invention, the polyether ionophore is administered to the subject at a total dosage quantity per dose selected from the group consisting of: 1 mg, 10 mg, 20 mg, 30 mg, 40 mg, 50 mg, 60 mg, 70 mg, 80 mg, 90 mg and 100 mg. In one embodiment of the invention, the polyether ionophore is administered to the subject at a total dosage quantity per dose selected from the group consisting of: 100 mg, 200 mg, 300 mg, 400 mg, 500 mg, 600 mg, 700 mg, 800 mg, 900 mg and 1000 mg.

The microbe may be a prokaryote or a eukaryotic. Preferably, the microbe is a bacterial agent selected from the group comprising, but not limited to, *Staphyloccus* spp, *Streptocccus* spp, *Bacillus* spp, *Enterococcus* spp, *Listeria* spp, *Mycoplasma* spp, and anaerobic bacteria. The bacterial agent may be selected from the group comprising, but not limited to, *Staphylococcus epidermidis*, *Staphylococcus simulans*, *Staphylococcus felis*, *Staphylococcus xylosus*, *Staphylococcus chromogenes*, *Staphylococcus warneri*, *Staphylococcus haemolyticus*, *Staphylococcus sciuri*, *Staphylococcus saprophyticus*, *Staphylococcus hominis*, *Staphylococcus caprae*, *Staphylococcus cohnii* subsp. *cohnii*, *Staphylococcus cohnii* subsp. *urealyticus*, *Staphylococcus capitis* subsp. *capitis*, *Staphylococcus capitis* subsp. *urealyticus*, *Staphylococcus hyicus*, *Staphylococcus aureus*, *Staphylococcus pseudintermedius*, *Staphylococcus delphini*, *Staphylococcus schleiferi* subsp. *coagulans*, *Staphylococcus aureus* subsp. *anaerobius*, *Streptococcus uberis*, *Streptococcus agalactiae*, *Streptococcus dysgalactiae*, *Streptococcus pyogenes*, *Streptococcus bovis*, *Streptococcus equi* subsp. *zooepidemicus*, *Streptococcus equinus*, *Bacillus melaninogenicus*, *Bacillus pumilus*, *Bacillus licheniformis*, *Bacillus cereus*, *Bacillus subtilis*, *Bacillus anthracis*, *Enterococcus faecium*, *Enterococcus faecalis*, *Enterococcus durans*, *Listeria monocytogenes*, *Clostridium perfringens*, *Clostridium difficile*, *Actinomyces bovis*, *Propionibacterium acnes*, *Propionibacterium granulosum*, *Eubacterium*, *Peptococcus indolicus*, *Peptostreptococcus anaerobius*, and *Mycoplasma bovis*.

More preferably, the bacterial agent is selected from a group comprising *Staphylococcus aureus*, *Staphylococcus pseudintermedius*, *Streptococcus pyogenes*, and *Propionibacterium acnes*. For example, the bacterial agent is methicillin resistant *Staphylococcus aureus* (MRSA) or methicillin resistant *Staphylococcus pseudintermedius* (MRSP).

Most preferably, the bacterial agent is an antibiotic-sensitive strain or an antibiotic-resistant strain. Examples of antibiotic-resistant strains include MRSA, MRSP, and macrolide, tetracycline, fluoroquinolone or cephalosporin resistant *Staphylococcus* spp. In a preferred embodiment, the bacterial strain is MRSA and MRSP.

In one embodiment, the bacterial agent is selected from the group comprising, but not limited to, coagulase-negative staphylococci (CNS). Examples of coagulase-negative staphylococci (CNS) include *Staphylococcus epidermidis* (isolated from bovine mastitis), *Staphylococcus simulans* (isolated from bovine mastitis or feline dermatitis), *Staphylococcus felis* (isolated from feline dermatitis), *Staphylococcus xylosus* (isolated from bovine mastitis or bovine dermatitis), *Staphylococcus chromogenes* (isolated from bovine mastitis or caprine dermatitis), *Staphylococcus warneri* (isolated from caprine colonisation), *Staphylococcus haemolyticus* (isolated from caprine colonisation), *Staphylococcus sciuri* (isolated from porcine exudative epidermatitis), *Staphylococcus saprophyticus* (isolated from caprine colonisation), *Staphylococcus hominis* (isolated from porcine colonisation), *Staphylococcus caprae* (isolated from caprine colonisation), *Staphylococcus cohnii* subsp. *cohnii* (isolated from caprine colonisation), *Staphylococcus cohnii* subsp. *urealyticus* (isolated from caprine colonisation), *Staphylococcus capitis* subsp. *capitis* (isolated from bovine mastitis), *Staphylococcus capitis* subsp. *urealyticus* (isolated from bovine mastitis), and *Staphylococcus hyicus* (isolated from porcine exudative epidermatitis and bovine colonisation).

In another embodiment, the bacterial agent is selected from coagulase-positive staphylococci. For example, the bacterial agent may be selected from the group comprising, but not limited to *Staphylococcus aureus* (isolated from human, equine, porcine, bovine, avian, canine and feline colonisation, bovine and ovine mastitis, and from many animal species with dermatitis and post-operative wound infection), *Staphylococcus pseudintermedius* (Canine pyoderma, canine and feline colonisation, *Staphylococcus delphini* (Dolphin suppurative skin lesions), *Staphylococcus schleiferi* subsp. *coagulans* (Canine otitis externa, canine, feline colonisation), and *Staphylococcus aureus* subsp. *anaerobius* (Ovine lymphadenitis). In a most preferred embodiment, the bacterial agent is *Streptococcus aureus*, which may be obtained from many lineages, many host adapted, including livestock associated MRSA sequence type (ST) or clonal complex (CC) 398 and ST9; various human community associated CA-MRSA and hospital associated HA-MRSA).

In another embodiment, the bacterial agent is from the *Streptococcus* genus. For example, the bacterial agent may be selected from the group comprising, but not limited to, *Streptococcus uberis*, *Streptococcus agalactiae*, *Streptococcus dysgalactiae*, *Streptococcus pyogenes* and other β-haemolytic streptococci, *Streptococcus bovis*, *Streptococcus equi* subsp. *zooepidemicus*, and *Streptococcus equinus*.

In another embodiment, the bacterial agent is from the *Bacillus* genus. For example, the bacterial agent may be selected from the group comprising, but not limited to, *Bacillus melaninogenicus*, *Bacillus pumilus*, *Bacillus licheniformis*, *Bacillus cereus*, *Bacillus subtilis*, and *Bacillus anthracis*.

In another embodiment, the bacterial agent is from the *Enterococcus* genus. For example, the bacterial agent may be selected from the group comprising, but not limited to, Enterococcus faecium, Enterococcus faecalis, and *Enterococcus durans*. These bacteria may be isolated from bovine mastitis.

In another embodiment, the bacterial agent is from the *Listeria* genus. For example, the bacterial agent may be *Listeria monocytogenes*.

In another embodiment, the bacterial agent is anaerobic. For example, the bacterial agent may be selected from the group comprising, but not limited to, *Clostridium perfringens, Clostridium difficile, Actinomyces bovis, Propionibacterium acnes, Propionibacterium granulosum, Eubacterium, Peptococcus indolicus,* and *Peptostreptococcus anaerobius.*

In another embodiment, the microbe is from the *Mycoplasma* genus. For example, the microbe may be *Mycoplasma bovis*.

In another embodiment, the microbe is a fungus or yeast, such as a fungus or yeast selected from the group comprising, but not limited to, superfical and cutaneous mycoses, Dermatophytes which include a variety of species of *Trichophyton, Microsporum* and *Epidermophyton*, a variety of species of *Candida* and *Malassezia* (previously known as *Pityrosporum*).

In a preferred embodiment, the microbe is *Staphylococcus aureus*. In most preferred embodiment, the microbe is MRSA or MRSP.

It will be understood that polyether ionophores described herein are typically effective against gram-positive bacteria and a number of anaerobic bacteria, as well as Mycoplasma and fungi. The sensitivity of a microbe to the polyether ionophores described herein varies, dependent on the individual strain, but in general, gram-positive cocci and bacilli, as were some anaerobes such as *Clostridium, Eubacterium, Proprionobacterium, Mycobacterium,* and *Streptomyces* are also susceptible. Fungi and yeasts, such as *Sclerotinia sclerotiorum, Monila taxa, Phomopsis mall, Botrytis cineria, Trichthecium roseum,* and *Verticillium albo-atrum* may also exhibit sensitivity to the polyether ionophores described herein.

In one embodiment of the invention, there is provided a method of treating a microbial skin, nares, ear canal or eye infection in a human, the method including the step of topically administering a therapeutically effective amount of a polyether ionophore, or a therapeutically acceptable salt thereof, to the skin, nares, ear canal or eye of the human.

In another embodiment of the invention, there is provided a method of treating a microbial skin, nares, ear canal or eye infection in a canine, the method including the step of topically administering a therapeutically effective amount of a polyether ionophore, or a therapeutically acceptable salt thereof, to the skin, nares, ear canal or eye of the canine.

According to another aspect of the invention there is provided a pharmaceutical or veterinary antimicrobial composition comprising a therapeutically effective amount of a polyether ionophore, or a therapeutically acceptable salt thereof.

The pharmaceutical or veterinary antimicrobial composition may optionally include a pharmaceutically acceptable excipient or carrier. Preferably, the composition is adapted to treat a topical microbial infection.

In one embodiment, the composition comprises impurities, wherein the quantity of impurities as a percentage of the total weight of the composition is selected from the group consisting of: less than 20% impurities (by total weight of the composition); less than 15% impurities; less than 10% impurities; less than 8% impurities; less than 5% impurities; less than 4% impurities; less than 3% impurities; less than 2% impurities; less than 1% impurities: less than 0.5% impurities; less than 0.1% impurities. In one embodiment, the composition comprises microbial impurities or secondary metabolites, wherein the quantity of microbial impurities as a percentage of the total weight of the composition is selected from the group consisting of: less than 5%; less than 4%; less than 3%; less than 2%; less than 1% s; less than 0.5%; less than 0.1%; less than 0.01%; less than 0.001%. In one embodiment, the composition is sterile and stored in a sealed and sterile container. In one embodiment, the composition contains no detectable level of microbial contamination.

In one embodiment, the composition does not comprise zinc.

In one embodiment, the composition does not comprise a keratolytic agent.

In one embodiment, the composition has antibacterial activity. In one embodiment, the composition does not have antifungal activity. In one embodiment, the composition does not have antiviral activity.

The pharmaceutical composition of the invention may be used in the treatment or prevention of topical microbial carriage or infections in humans, such as a bacterial infection or carriage caused by bacteria of the *Staphylococcus* genus.

According a further aspect of the invention there is provided a veterinary antimicrobial composition comprising a therapeutically effective amount of a polyether ionophore, or a therapeutically acceptable salt thereof.

The composition may be administered topically.

The veterinary composition may optionally include a pharmaceutically acceptable excipient or carrier.

The composition of the invention may be provided in a form selected from the group comprising, but not limited to, a rinse, a shampoo, a lotion, a gel, a leave-on preparation, a wash-off preparation, and an ointment. Preferably, the composition is selected from the group consisting of: an immediate release composition, a delayed release composition, a controlled release composition and a rapid release composition.

The composition of the invention may comprise a further antimicrobial agent. The further antimicrobial agent may be an antifungal agent.

In one embodiment, the antifungal agent is selected from the group comprising, but not limited to, Echinocandins (Anidulafungin, Caspofungin, Micafungin), Polyenes (Amphotericin B, Candicidin, Filipin, Fungichromin, Hachimycin, Hamycin, Lucensomycin, Mepartricin, Natamycin, Nystatin, Pecilocin, Perimycin, Griseofulvin, Oligomycins, Pyrrolnitrin, Siccanin, and Viridin. The antifungal agent may be a synthetic compound selected from the group comprising, but not limited to, Allylamines (Butenafine, Naftifine, Terbinafine) Imidazoles (Bifonazole, Butoconazole, Chlormidazole, Cloconazole, Clotrimazole, Econazole, Fenticonazole, Flutrimazole, Isoconazole, Ketoconazole, Lanoconazole, Miconazole, Neticonazole, Omoconazole, Oxiconazole Nitrate, Sertaconazole, Sulconazole, Tioconazole), Thiocarbamates (Liranaftate, Tolciclate, Tolindate, Tolnaftate), Triazoles (Fluconazole, Isavuconazole, Itraconazole, Posaconazole, Ravuconazole, Saperconazole, Terconazole, Voriconazole), Acrisorcin, Amorolfine, Bromosalicylchloranilide, Buclosamide, Calcium Propionate, Chlorphenesin, Ciclopirox, Cloxyquin, Coparaffinate, Exalamide, Flucytosine, Haloprogin, Hexetidine, Loflucarban, Nifuratel, Potassium Iodide, Propionic Acid, Pyrithione, Salicylanilide, Sodium Propionate, Sulbentine, Tenonitrozole, Triacetin, Undecylenic Acid, and Zinc Propionate.

In another embodiment, the antifungal agent is selected from the group comprising, but not limited to, Amorolfine, Amphotericin B, Anidulafungin, Bifonazole, Bromochlorosalicylanilide, Butenafine Hydrochloride, Butoconazole Nitrate, Caspofungin Acetate, Chlormidazole Hydrochloride, Chlorphenesin, Ciclopirox, Climbazole, Clotrimazole, Cloxiquine, Croconazole Hydrochloride, Eberconazole Nitrate, Econazole, Enilconazole, Fenticonazole Nitrate, Fluconazole, Flucytosine, Flutrimazole, Fosfluconazole, Griseofulvin, Isoconazole, Itraconazole, Ketoconazole, Lanoconazole, Liranaftate, Luliconazole, Mepartricin, Micafungin Sodium, Miconazole, Naftifine Hydrochloride, Natamycin, Neticonazole Hydrochloride, Nifuroxime, Nystatin, Omoconazole Nitrate, Oxiconazole Nitrate, Parconazole Hydrochloride, Pentamycin, Piroctone olamine, Posaconazole, Propionic Acid, Pyrrolnitrin, Ravuconazole, Sertaconazole Nitrate, Siccanin, Sodium Parachlorobenzoate, Sulconazole Nitrate, Terbinafine, Terconazole, Tioconazole, Tolciclate, Tolnaftate, Triacetin, Trimetrexate Glucuronate, Undecenoic Acid and Voriconazole The composition of the invention may comprise an antibiotic adjunct selected from the group comprising, but not limited to, β-Lactamase Inhibitors (Clavulanic Acid, Sulbactam, Sultamicillin, Tazobactam), Renal Dipeptidase Inhibitors (Cilastatin), and Renal Protectant (Betamipron).

In one embodiment, the composition of the invention comprises a further antibiotic selected from the group comprising, but not limited to, Aminoglycosides (Amikacin, Arbekacin, Bambermycins, Butirosin, Dibekacin, Dihydrostreptomycin, Fortimicins, Gentamicin, Isepamicin, Kanamycin, Micronomicin, Neomycin, Netilmicin, Paromomycin, Ribostamycin, Sisomicin, Spectinomycin, Streptomycin, Tobramycin), Amphenicols (Azidamfenicol, Chloramphenicol, Thiamphenicol) Ansamycins (Rifamide, Rifampin, Rifamycin SV, Rifapentine, Rifaximin), β-Lactams, Carbacephems (Loracarbef) Carbapenems (Biapenem, Doripenem, Ertapenem, Imipenem, Meropenem, Panipenem), Cephalosporins (Cefaclor, Cefadroxil, Cefamandole, Cefatrizine, Cefazedone, Cefazolin, Cefcapene, Cefdinir, Cefditoren, Cefepime, Cefetamet, Cefixime, Cefmenoxime, Cefodizime, Cefonicid, Cefoperazone, Ceforanide, Cefoselis, Cefotaxime, Cefotiam, Cefozopran, Cefpimizole, Cefpiramide, Cefpirome, Cefpodoxime, Cefprozil, Cefroxadine, Cefsulodin, Ceftaroline, Ceftazidime, Cefteram, Ceftezole, Ceftibuten, Ceftizoxime, Ceftobiprole Medocaril, Ceftriaxone, Cefuroxime, Cefuzonam, Cephacetrile, Cephalexin, Cephaloglycin, Cephaloridine, Cephalothin, Cephapirin, Cephradine, Pivcefalexin), Cephamycins (Cefbuperazone, Cefmetazole, Cefminox, Cefotetan, Cefoxitin), Monobactams (Aztreonam, Carumonam), Oxacephems (Flomoxef, Moxalactam), Penems (Faropenem, Ritipenem), Penicillins (Amdinocillin, Amdinocillin Pivoxil, Amoxicillin, Ampicillin, Apalcillin, Aspoxicillin, Azidocillin, Azlocillin, Bacampicillin, Carbenicillin, Carindacillin, Clometocillin, Cloxacillin, Cyclacillin, Dicloxacillin, Epicillin, Fenbenicillin, Floxacillin, Hetacillin, Lenampicillin, Metampicillin, Methicillin Sodium, Mezlocillin, Nafcillin, Oxacillin, Penamecillin, Penethamate Hydriodide, Penicillin G, Penicillin G Benzathine, Penicillin G Procaine, Penicillin N, Penicillin O, Penicillin V, Phenethicillin Potassium, Piperacillin, Pivampicillin, Propicillin, Quinacillin, Sulbenicillin, Sultamicillin, Talampicillin, Temocillin, Ticarcillin), Lincosamides (Clindamycin, Lincomycin), Macrolides (Azithromycin, Cethromycin, Clarithromycin, Dirithromycin, Erythromycin, Erythromycin Acistrate, Erythromycin Estolate, Erythromycin Glucoheptonate, Erythromycin Lactobionate, Erythromycin Propionate, Erythromycin Stearate, Fidaxomicin, Josamycin, Leucomycin, Midecamycins, Miokamycin, Oleandomycin, Primycin, Rokitamycin, Rosaramicin, Roxithromycin, Spiramycin, Telithromycin, Troleandomycin), Polypeptides (Amphomycin, Bacitracin, Bacitracin Zinc, Capreomycin, Colistin, Dalbavancin, Daptomycin, Enduracidin, Enviomycin, Fusafungine, Gramicidin(s), Gramicidin S, Iseganan, Oritavancin, Polymyxin, Quinupristin, Ramoplanin, Ristocetin, Teicoplanin, Telavancin, Thiostrepton, Tuberactinomycin, Tyrocidine, Tyrothricin, Vancomycin, Viomycin), Tetracyclines (Chlortetracycline, Clomocycline, Demeclocycline, Doxycycline, Guamecycline, Lymecycline, Meclocycline, Methacycline, Minocycline, Oxytetracycline, Pipacycline, Rolitetracycline, Tetracycline, Tigecycline), Others (Cycloserine, Dalfopristin, Fosfomycin, Fusidic Acid, Mupirocin, Pristinamycin, Retapamulin and Virginiamycin).

In another embodiment, the composition of the invention further comprises a synthetic antibiotic selected from the group comprising, but not limited to, 2,4-Diaminopyrimidines (Brodimoprim, Iclaprim, Tetroxoprim, Trimethoprim), Nitrofurans (Furaltadone, Furazolium Chloride, Nifuratel, Nifurfoline, Nifurpirinol, Nifurtoinol, Nitrofurantoin) Oxazolidinones (Linezolid), Peptides (Omiganan, Pexiganan), Quinolones and Analogs (Balofloxacin, Besifloxacin, Cinoxacin, Ciprofloxacin, Clinafloxacin, Enoxacin, Finafloxacin, Fleroxacin, Flumequine, Garenoxacin, Gatifloxacin, Gemifloxacin, Grepafloxacin, Lomefloxacin, Miloxacin, Moxifloxacin, Nadifloxacin, Nalidixic Acid, Norfloxacin, Ofloxacin, Oxolinic Acid, Pazufloxacin, Pefloxacin, Pipemidic Acid, Piromidic Acid, erulifloxacin, Rosoxacin, Rufloxacin, Sitafloxacin, Sparfloxacin, Tosufloxacin, Trovafloxacin), Sulfonamides (Acetyl Sulfamethoxypyrazine, Chloramine-B, Chloramine-T, Dichloramine T, Mafenide, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadoxine, Sulfaethidole, Sulfaguanidine, Sulfaguanole, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, N4-Sulfanilylsulfanilannide, Sulfanilylurea, N-Sulfanilyl-3,4-xylamide, Sulfaperine, Sulfaphenazole, Sulfaproxyline, Sulfapyrazine, Sulfapyridine, Sulfathiazole, Sulfathiourea, Sulfisomidine, Sulfisoxazole), Sulfones (Acediasulfone, Dapsone, Glucosulfone Sodium, Succisulfone, Sulfanilic Acid, p-Sulfanilylbenzylamine, Sulfoxone Sodium, Thiazolsulfone), Clofoctol, Methenamine, Metronidazole, Nitroxoline, Taurolidine, and Xibornol.

In another embodiment, the composition of the invention further comprises an antibiotic selected from the group comprising, but not limited to, Acediasulfone Sodium, Amikacin, Aminosalicylic Acid, Amoxicillin, Ampicillin, Apramycin, Arbekacin Sulfate, Arsanilic Acid, Aspoxicillin, Astromicin Sulfate, Avilamycin, Avoparcin, Azidamfenicol, Azidocillin Sodium, Azithromycin, Azlocillin, Aztreonam, Bacampicillin Hydrochloride, Bacitracin, Balofloxacin, Bambermycin, Baquiloprim, Bekanamycin Sulfate, Benethamine Penicillin, Benzathine Benzylpenicillin, Benzathine Phenoxymethylpenicillin, Benzylpenicillin, Besifloxacin, Betamipron, Biapenem, Brodimoprim, Capreomycin Sulfate, Carbadox, Carbenicillin Sodium, Carindacillin Sodium, Carumonam Sodium, Cefaclor, Cefadroxil, Cefalexin, Cefalonium, Cefaloridine, Cefalotin Sodium, Cefamandole, Cefapirin Sodium, Cefatrizine, Cefazolin, Cefbuperazone, Cefcapene Pivoxil Hydrochloride, Cefdinir, Cefditoren Pivoxil, Cefepime Hydrochloride, Cefetamet, Cefixime, Cefmenoxime Hydrochloride, Cefmetazole, Cefminox Sodium, Cefodizime Sodium, Cefonicid Sodium, Cefoperazone Sodium, Ceforanide, Cefoselis Sulfate, Cefotaxime Sodium, Cefotetan, Cefotiam Hydrochloride, Cefovecin Sodium, Cefoxitin Sodium, Cefozopran Hydrochloride, Cefpiramide, Cefpirome Sulfate, Cefpodoxime Proxetil, Cefprozil, Cefquinome Sulfate, Cefradine, Cefsulodin Sodium, Ceftaroline Fosamil Acetate, Ceftazidime, Cefteram Pivoxil, Ceftezole Sodium, Ceftibuten, Ceftiofur, Ceftizoxime Sodium, Ceftobiprole Medocaril, Ceftriaxone Sodium, Cefuroxime, Cethromycin, Chloramphenicol, Chloroxine, Chlorquinaldol, Chlortetracycline, Ciclacillin, Cilastatin Sodium, Cinoxacin, Ciprofloxacin, Clarithromycin, Clavulanic Acid, Clemizole Penicillin, Clindamycin, Clioquinol, Clofazimine, Clofoctol, Clometocillin Potassium, Cloxacillin, Colistin Sulfate, Co-tetroxazine, Co-trifamole, Co-trimoxazole, Cycloserine, Dalbavancin, Danofloxacin Mesilate, Dapsone, Daptomycin, Delamanid, Demeclocycline, Dibekacin Sulfate, Dicloxacillin, Difloxacin Hydrochloride, Dihydrostreptomycin Sulfate, Dirithromycin, Doripenem, Doxycycline, Enoxacin, Enrofloxacin, Ertapenem Sodium, Euthromycin, Ethambutol Hydrochloride, Ethionamide, Etimicin Sulfate, Faropenem Sodium, Fidaxomicin, Fleroxacin, Flomoxef Sodium, Florfenicol, Flucloxacillin, Flumequine, Flurithromycin Ethyl Succinate, Formosulfathiazole, Fosfomycin, Framycetin Sulfate, Ftivazide, Furaltadone Hydrochloride, Furazidin, Fusafungine, Fusidic Acid, Gamithromycin, Garenoxacin Mesilate, Gatifloxacin, Gemifloxacin Mesilate, Gentamicin Sulfate, Gramicidin, Gramicidin S, Halquinol, Ibafloxacin, Iclaprim, Imipenem, Isepamicin, Isoniazid, Josamycin, Kanamycin Acid Sulfate, Kitasamycin, Latamoxef Disodium, Levofloxacin, Lincomycin, Linezolid, Lomefloxacin Hydrochloride, Loracarbef, Lymecycline, Mafenide, Magainins, Mandelic Acid, Marbofloxacin, Mecillinam, Meclocycline, Meleumycin, Meropenem, Methacycline, Methenamine, Meticillin Sodium, Mezlocillin, Micronomicin Sulfate, Midecamycin, Minocycline, Morinamide, Moxifloxacin Hydrochloride, Mupirocin, Nadifloxacin, Nafcillin Sodium, Nalidixic Acid, Neomycin, Netilmicin Sulfate, Nifuroxazide, Nifurpirinol, Nifurtoinol, Nifurzide, Nisin, Nitrofurantoin, Nitrofurazone, Nitroxoline, Norfloxacin, Norvancomycin Hydrochloride, Novobiocin, Ofloxacin, Oleandomycin Phosphate, Orbifloxacin, Oritavancin, Ormetoprim, Oxacillin Sodium, Oxolinic Acid, Oxytetracycline, Panipenem, Pazufloxacin Mesilate, Pefloxacin Mesilate, Penethamate Hydriodide, Pheneticillin Potassium, Phenoxymethylpenicillin, Phthalylsulfacetamide, Phthalylsulfathiazole, Pipemidic Acid, Piperacillin, Pirlimycin Hydrochloride, Piromidic Acid, Pivampicillin, Pivmecillinam, Polymyxin B Sulfate, Pradofloxacin, Pristinamycin, Procaine Benzylpenicillin, Propicillin Potassium, Protionamide, Prulifloxacin, Pyrazinamide, Quinupristin/Dalfopristin, Ramoplanin, Retapamulin, Ribostamycin Sulfate, Rifabutin, Rifampicin, Rifamycin Sodium, Rifapentine, Rifaximin, Rokitamycin, Rolitetracycline, Rosoxacin, Roxithromycin, Rufloxacin Hydrochloride, Sarafloxacin Hydrochloride, Sisomicin Sulfate, Sitafloxacin, Sparfloxacin, Spectinomycin, Spiramycin, Streptomycin, Succinylsulfathiazole, Sulbactam, Sulbenicillin Sodium, Sulfabenzamide, Sulfacarbamide, Sulfacetamide, Sulfachlorpyridazine, Sulfachrysoidine, Sulfaclozine, Sulfadiazine, Sulfadiazine Silver, Sulfadicramide, Sulfadimethoxine, Sulfadimidine, Sulfadoxine, Sulfafurazole, Sulfaguanidine, Sulfamerazine, Sulfamethizole, Sulfamethoxazole, Sulfamethoxypyridazine, Sulfamethylthiazole, Sulfametopyrazine, Sulfametrole, Sulfamonomethoxine, Sulfamoxole, Sulfanilamide, Sulfapyridine, Sulfaquinoxaline, Sulfathiazole, Sulfathiazole Silver, Sulfatroxazole, Sulfisomidine, Sultamicillin, Taurolidine, Tazobactam Sodium, Teicoplanin, Telavancin, Telithromycin, Temocillin, Terizidone, Tetracycline, Tetroxoprim, Thenoic Acid, Thiamphenicol, Thioacetazone, Thiostrepton, Tiamulin, Ticarcillin Monosodium, Tigecycline, Tildipirosin, Tilmicosin, Tobramycin, Tosufloxacin, Trimethoprim, Troleandomycin, Tulathromycin, Tylosin, Tylvalosin Tartrate, Tyrothricin, Valnemulin, Vancomycin, Virginiamycin, and Xibornol.

Preferably, the composition of the invention comprises a further antibiotic selected from the group comprising, but not limited to, penicillin G, penethamate, cloxacillin, nafcillin, ampicillin, amoxycillin, clavulanic acid, streptomycin, neomycin, framycetin, tetracycline, gentamicin, fluoroquinolones and polymyxins.

The composition of the veterinary composition of the invention may further comprise an excipient selected from the group comprising, but not limited to, binders and compression aids, coatings and films, colouring agents diluents and vehicles disintegrants, emulsifying and solubilising agents, flavours and sweeteners, repellents, glidants and lubricants, plasticisers, preservatives, propellants, solvents, stabilisers, suspending agents and viscosity enhancers. In an embodiment of the invention, the composition further comprises a chelating agent, such as citric acid, EDTA or maltol. It will be understood that such excipients may result in any change of the pH of the composition.

In one embodiment, the composition is an ointment comprising polyether ionophore, paraffin oil and Vaseline. For example, the composition is:

| Paraffin oil | 49.0 g |
|---|---|
| Vaseline | 49.0 g |
| Ionophore | 2.0 g |

In one embodiment, the composition is an ointment comprising polyether ionophore, lanolin, preservative, paraffin oil and Vaseline. For example, the composition is:

| Lanolin | 10.0 g |
|---|---|
| Vaseline | 80.0 g |
| Parafin oil | 7.9 g |
| Preservative | 0.1 g |
| Ionophore (2%) | 2.0 g |

In one embodiment, the composition is a gel comprising polyether ionophore, polyethylene glycol (PEG), glycerol, and distilled water. For example, the composition is:

| PEG 4000 | 35.0 g |
|---|---|
| PEG 200 | 40.0 g |
| Glycerol | 6.0 g |
| Distilled water | 17.0 g |
| Ionophore | 2.0 g |

In one embodiment, the composition is a cream comprising polyether ionophore, glycerol monostearate, preservative, paraffin oil, stearate acid, potassium stearate, glycerol, distilled water and Vaseline. For example, the composition is:

| | |
|---|---|
| Glycerol monostearate | 12.0 g |
| Vaseline | 15.0 g |
| Stearate acid | 1.3 g |
| Paraffin oil | 5.0 g |
| Potassium stearate | 0.7 g |
| Glycerol | 10.0 g |
| Preservative | 0.1 g |
| Ionophore (2%) | 2.0 g |
| Distilled water | to 100 g |

According to a further aspect of the invention, there is provided a medical or veterinary device when used in a method of treating or preventing a topical microbial infection in the subject.

According to further aspect of the invention, there is provided a medical device comprising the composition of the invention.

The medical device may be in a form selected from the group comprising a plaster, a bandage, and other dressing applied to a localised microbial infection on the skin, nares, ear canal or eye of a subject.

In a further aspect, the invention is the use of a polyether ionophore, or a therapeutically acceptable salt thereof, in the manufacture of medicament for the treatment of a topical microbial condition in a subject. Preferably, the use comprises administering a therapeutically effective amount of a polyether ionophore, or a therapeutically acceptable salt thereof, to the subject.

In a further aspect, the invention is a method, a composition, a device, or a use, substantially as described herein with reference to the accompanying examples and figures.

In a further aspect, the invention is the composition according to claim 16, the device according to claim 26, and the use according to claim 29, substantially as described herein with reference to the accompanying examples and figures.

Terms used herein will have their customary meanings in the art unless specified. As set out herein, the following terms refer to the polyether ionophores indicated:

In regards to the Examples and Figures, LP 1088 refers to Salinomycin; LP 1369 refers to Lasalocid; LP 4525 refers to Narasin; LP 6315 refers to Maduramicin; and LP 9666 refers to Monensin.

As used herein, the term lasalocid, (also known as Avatec, Bovatec, Antibiotic X-537A, Ionophore X-4537A, and Ro 2-2985, CAS registry number 25999-31-9 (acid), 25999-20-6 (Na salt)) refers to a compound having the following chemical structure:

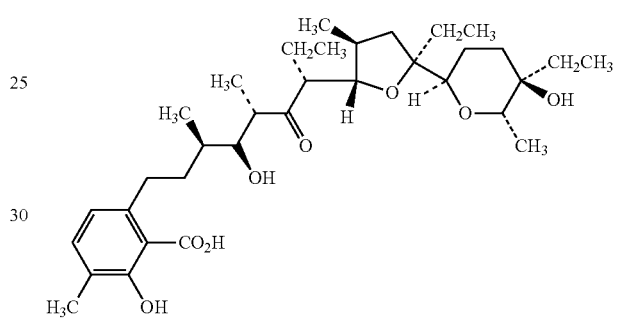

As used herein, the term monensin, (also known as Coban, Rumensin, Monensic acid, and A 3823A, CAS registry number 17090-79-8 (acid), 22373-78-0 (Na salt)) refers to a compound having the following chemical structure:

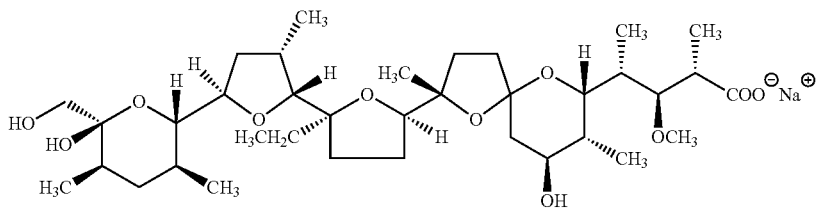

As used herein, the term salinomycin, (also known as Coxistac, Posistac, Salocin, Ovicox, AHR-3096, K-364, and K-748364A, CAS registry number 53003-10-4 (acid), 55721-31-8 (Na salt)) refers to a compound having the following chemical structure:

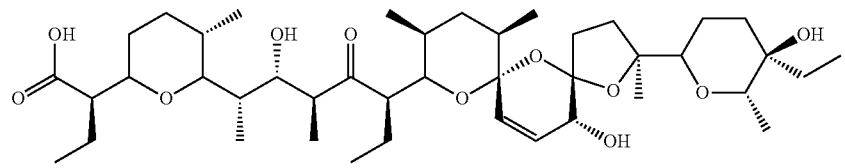 [SMILES: CC[C@@H](C(=O)O)C1CC[C@H](C)C([C@@H](C)[C@H](O)[C@H](C)C(=O)[C@H](CC)C2O[C@]3(C=C[C@@H](O)[C@]4(CC[C@@](C)(C5CC[C@](O)(CC)[C@H](C)O5)O4)O3)[C@H](C)C[C@@H]2C)O1]

As used herein, the term narasin, (also known as Monteban, 4-methylsalinomycin, Compound 79891, A-28086 factor A, C-7819B, CAS registry number 55134-13-9 (acid)) refers to a compound having the following chemical structure:

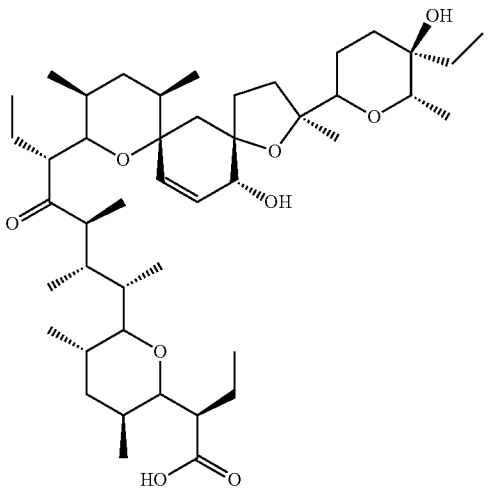 [SMILES: CC[C@@H](C(=O)O)C1OC([C@@H](C)[C@H](C)[C@H](C)C(=O)[C@H](CC)C2O[C@]3(C=C[C@@H](O)[C@]4(CC[C@@](C)(C5CC[C@](O)(CC)[C@H](C)O5)O4)C3)[C@H](C)C[C@@H]2C)[C@@H](C)C[C@@H]1C]

As used herein, the term maduramicin refers to a compound having the following chemical structure (represented below as maduramicin ammonium):

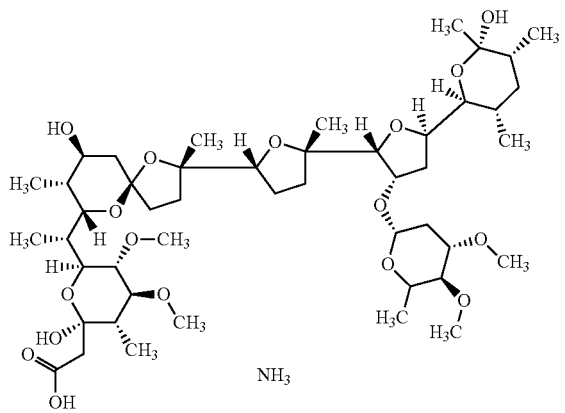

It is an advantage of the invention that the compositions described are applied in a method of treatment of a topical microbial infection, such as a microbial skin infection. The outermost layers of the skin of a mammal constitute a physical barrier to the absorption of many therapeutic substances. The stratum corneum of the skin functions as a physical barrier to the absorption of toxic substances. Topical application of the compositions of the invention is designed to result in a localised treatment of an infected site on the skin of a subject by way of exposure to a polyether ionophore, with minimal systemic absorption through the skin by the subject. In this way, therapeutically effective amounts of a polyether ionophore may be applied in the treatment of a microbial infection of the skin without exposing the subject to substantially toxic doses of the substance.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIGS. 1A-1B are a table setting out the isolate collection and the vertebrate species source following biochemical identification of the *Staphylococcus* species including resistance profile according to Example 1;

FIG. 5 shows a table illustrating the $MIC_{50}$, $MIC_{90}$ and MIC ranges for the methicillin-sensitive isolates for ampicillin and the five test compounds according to Example 1;

FIG. 6 shows a table illustrating the $MIC_{50}$, $MIC_{90}$ and MIC ranges for the methicillin-resistant isolates for ampicillin and the five test compounds according to Example 1;

FIG. 21 is a table setting out the isolate collection and the dog breed source following biochemical identification of the *Staphylococcus pseudintermedius* isolates including resistance profile according to Example 2;

FIGS. 22A-22B are a table setting out the resistance profile of the *Staphylococcus pseudintermedius* isolates collected according to Example 2;

FIG. 23 is a table setting out the MIC profile of ampicillin and LP compounds of the *Staphylococcus pseudintermedius* isolates collected according to Example 2;

FIG. 27 is a table showing the $MIC_{50}$, $MIC_{90}$, MIC range and $MBC_{50}$, $MBC_{90}$, and MBC range of each compound tested against six coagulase-negative *Staphylococcus aureus* isolates according to Example 3;

FIG. 28 is a table showing the $MIC_{50}$, $MIC_{90}$, MIC range and $MBC_{50}$, $MBC_{90}$, and MBC range of each compound tested against 12 *Staphylococcus agalactiae* isolates according to Example 3;

FIG. 29 is a table showing the $MIC_{50}$, $MIC_{90}$, MIC range and $MBC_{50}$, $MBC_{90}$, and MBC range of each compound tested against six *Staphylococcus uberis* isolates according to Example 3;

FIGS. 30A-30D are a table showing the profiles of the bovine mastitis isolates according to Example 3;

FIG. 31 is a table showing the MICs of individual bovine mastitis isolates according to Example 3;

FIG. 32 is a table showing the MBCs of individual bovine mastitis isolates according to Example 3;

FIGS. 34A-34B include two tables presenting the group statistics (FIG. 34A) and a graph presenting the results of the study presented in Example 5 (FIG. 34B).

DESCRIPTION OF EMBODIMENTS

General

Figure 2:
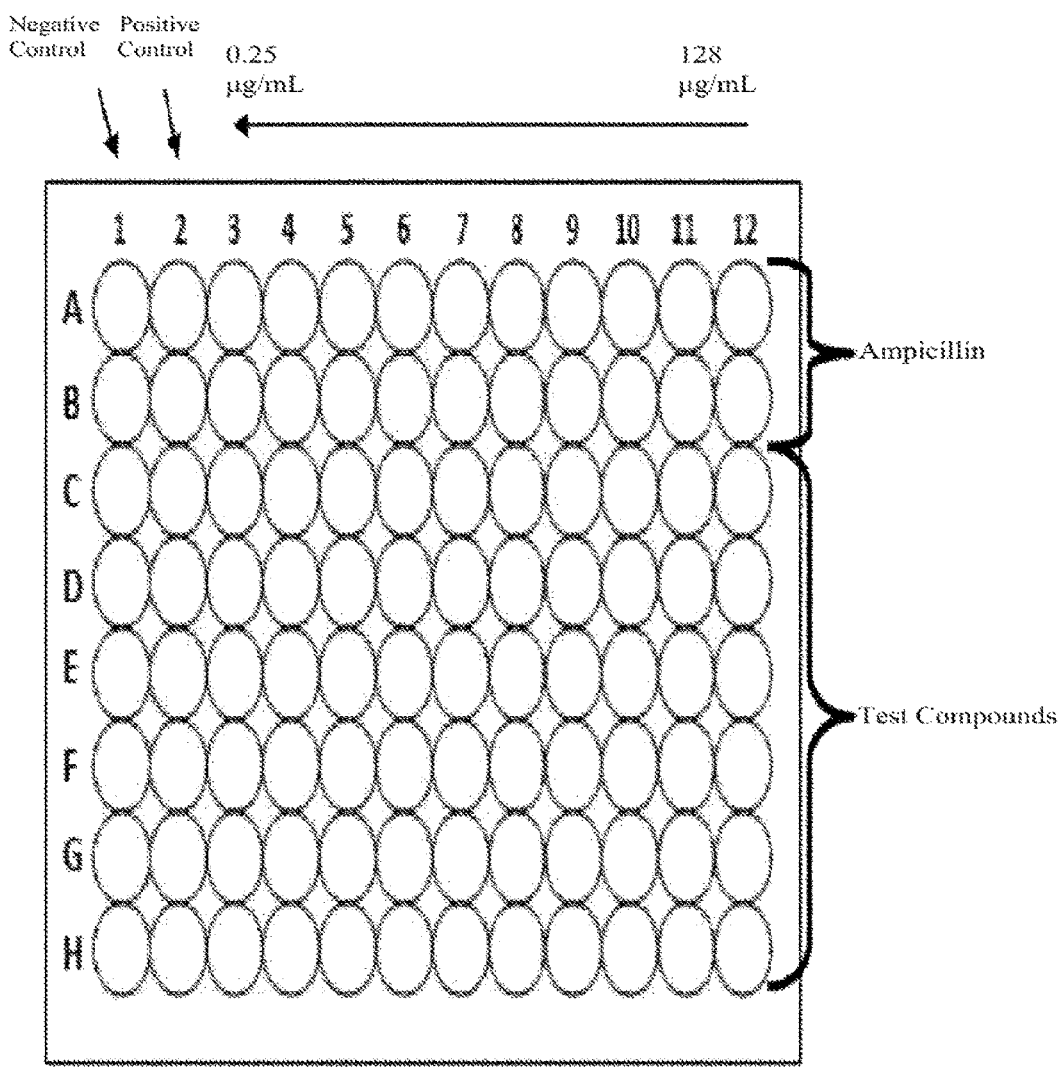
FIG. 2 is a diagrammatic representation of the 96 well plate layout for the Minimum Inhibitory Concentration Testing according to Example 1.

Before describing the present invention in detail, it is to be understood that the invention is not limited to particular exemplified methods or compositions disclosed herein. It is also to be understood that the terminology used herein is for the purpose of describing particular embodiments of the invention only, and is not intended to be limiting.

All publications referred to herein, including patents or patent applications, are incorporated by reference in their entirety. However, applications that are mentioned herein are referred to simply for the purpose of describing and disclosing the procedures, protocols, and reagents referred to in the publication which may have been used in connection with the invention. The citation of any publications referred to herein is not to be construed as an admission that the invention is not entitled to antedate such disclosure by virtue of prior invention.

In addition, the carrying out of the present invention makes use of, unless otherwise indicated, conventional microbiological techniques within the skill of the art. Such conventional techniques are known to the skilled worker.

As used herein, and in the appended claims, the singular forms "a", "an", and "the" include the plural unless the context clearly indicates otherwise.

Unless otherwise indicated, all technical and scientific terms used herein have the same meanings as commonly understood by one of ordinary skill in the art to which this invention belongs. Although any materials and methods similar to, or equivalent to, those described herein may be used to carry out the present invention, the preferred materials and methods are herein described.

The invention described herein may include one or more ranges of values (e.g. size, concentration, dose etc). A range of values will be understood to include all values within the range, including the values defining the range, and values adjacent to the range that lead to the same or substantially the same outcome as the values immediately adjacent to that value which define the boundary of the range.

The phrase "therapeutically effective amount" as used herein refers to an amount sufficient to inhibit bacterial growth associated with bacterial carriage or a bacterial infection of the skin. That is, reference to the administration of the therapeutically effective amount of polyether ionophores according to the methods or compositions of the invention refers to a therapeutic effect in which substantial bacteriocidal or bacteriostatic activity causes a substantial inhibition of the bacterial carriage or bacterial infection of the skin. The term "therapeutically effective amount" as used herein, refers to a nontoxic but sufficient amount of the composition to provide the desired biological, therapeutic, and/or prophylactic result. The desired results include elimination of bacterial carriage or reduction and/or alleviation of the signs, symptoms, or causes of a disease, or any other desired alteration of a biological system. An effective amount in any individual case may be determined by one of ordinary skill in the art using routine experimentation. In relation to a pharmaceutical or veterinary composition, effective amounts can be dosages that are recommended in the modulation of a diseased state or signs or symptoms thereof. Effective amounts differ depending on the pharmaceutical or veterinary composition used and the route of administration employed. Effective amounts are routinely optimized taking into consideration various factors of a particular patient, such as age, weight, gender, etc and the area affected by disease or disease causing microorganisms.

As referred to herein, the terms "microbe" and "microbial" refers to a microscopic organism comprising either a single cell wall clusters of cells and encompasses, but is not limited to, prokaryotes such as bacteria and archaea; and forms of eukaryotes such as protozoan, fungi, algae. Preferably the terms "microbe" and "microbial" refers to prokaryotes and eukaryotes. The prokaryotes may refer to bacteria, such as *Staphylococcus* spp, *Streptocccus* spp, *Bacillus* spp, *Enterococcus* spp, *Listeria* spp, *Mycoplasma* spp, and anaerobic bacteria. The terms may refer to an antibiotic-sensitive strain or an antibiotic-resistant strain. In a preferred embodiment, the terms refer to MRSA. In another preferred embodiment, the terms refer to MRSP.

In one embodiment, the terms "microbe" and "microbial" refer to one or more of coagulase-negative staphylococci (CNS): *Staphylococcus epidermidis. Staphylococcus simulans, Staphylococcus fells, Staphylococcus xylosus, Staphylococcus chromogenes, Staphylococcus warneri, Staphylococcus haemolyticus, Staphylococcus sciuri, Staphylococcus saprophyticus, Staphylococcus hominis, Staphylococcus caprae), Staphylococcus cohnii* subsp. *Cohnii, Staphylococcus cohnii* subsp. *urealyticus, Staphylococcus capitis* subsp. *capitis, Staphylococcus capitis* subsp. *urealyticus*, and *Staphylococcus hyicus*.

In another embodiment, the terms "microbe" and "microbial" refer to one or more of coagulase-positive staphylococci: *Staphylococcus aureus, Staphylococcus pseudintermedius, Staphylococcus delphini, Staphylococcus schleiferi* subsp. *Coagulans*, and *Staphylococcus aureus* subsp. *anaerobius*.

In another embodiment, the bacterial agent is from the *Streptococcus* genus. For example, the bacterial agent may be selected from the group comprising, but not limited to, *Streptococcus uberis, Streptococcus agalactiae, Streptococcus dysgalactiae, Streptococcus pyogenes, Streptococcus bovis, Streptococcus equi* subsp. *Zooepidemicus*, and *Streptococcus equinus*.

In another embodiment, the terms "microbe" and "microbial" refer to one or more of bacterial agent of the *Baccillus* genus: *Bacillus melaninogenicus, Bacillus pumilus, Bacillus licheniformis, Bacillus cereus, Bacillus subtilis*, and *Bacillus anthracis*.

In another embodiment, the terms "microbe" and "microbial" refer to one or more of bacterial agent of the *Enterococcus* genus: *Enterococcus faecium, Enterococcus faecalis*, and *Enterococcus durans*.

In another embodiment, the terms "microbe" and "microbial" refer to one or more of bacterial agent of the *Listeria* genus: such as *Listeria monocytogenes*.

In another embodiment, the terms "microbe" and "microbial" refer to one or more anaerobic bacteria: *Clostridium perfringens, Actinomyces bovis, Propionibacterium acnes, Propionibacterium granulosum, Eubacterium, Peptococcus indolicus*, and *Peptostreptococcus anaerobius*.

In another embodiment, the terms "microbe" and "microbial" refer to one or more species of the *Mycoplasma* genus: such as *Mycoplasma bovis*.

In another embodiment, the terms "microbe" and "microbial" refer to one or more fungi of the *Malassezia* genus.

In another embodiment, the terms "treatment" or "treating" refers to the full or partial removal of the signs and symptoms of the condition. For example, in the treatment of a skin condition, the treatment completely or partially removes the symptoms of the skin condition. Preferably in the treatment of a skin, ear canal or eye condition, the treatment reduces the *Staphylococcus aureus* cell count below $10^{6.5}$ cells/mL. Preferably in the treatment of a skin, ear canal or eye condition, the treatment reduces the pathogenic microbial cell count below $10^{6.5}$ cells/mL which represents a percentage reduction from the pretreatment level selected from the group consisting of: by 10%; by 20%; by 50%; by 80%; by 90%, by 95%, by 99% and by >99%.

Pharmaceutically or veterinary acceptable salts include salts which retain the biological effectiveness and properties of the compounds of the present disclosure and which are not biologically or otherwise undesirable. In many cases, the compounds disclosed herein are capable of forming acid and/or base salts by virtue of the presence of amino and/or carboxyl groups or groups similar thereto. Pharmaceutically or veterinary acceptable base addition salts can be prepared from, inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as by way of example only, alkyl amines, dialkyl amines, trialkyl amines, substituted alkyl amines, di(subsrituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amines, trisubstituted cycloalkyl amines, cycloalkenyl amines, di(cycloalkenyl) amines, tri(cycloalkenyl) amines, substituted cycloalkenyl amines, disubstituted cycloalkenyl amines, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Pharmaceutically or veterinary acceptable acid addition salts may be prepared from inorganic and organic acids. The inorganic acids that can be used include, by way of example only, hydrochloric acid, hydrobromic acid, sulfuric acid, nitric acid, phosphoric acid, and the like. The organic acids that can be used include, by way of example only, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The pharmaceutically or veterinary acceptable salts of the compounds useful in the present disclosure can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences. 17th ed., Mack Publishing Company, Easton, Pa. (1985), p. 1418, the disclosure of which is hereby incorporated by reference. Examples of such pharmaceutically or veterinary acceptable salts are the iodide, acetate, phenyl acetate, trifluoroacetate, acryl ate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, γ-hydroxybutyrate, β-hydroxybutyrate, butyne-1,4-dioate, hexyne-1,4-dioate, hexyne-1,6-dioate, caproate, caprylate, chloride, cinnamate, citrate, decanoate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, propanesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

It will be understood that the type of microbial carriage and infections for which the methods of the invention are intended to be used in treatment include nasal carriage or colonisation, skin or skin structure infections, wound infections, and any other superficial microbial infections affecting the skin. Such skin infections encompass but are not limited to acne, impetigo, folliculitis, furunculosis, and carbunculosis, ecthyma, erysipelas and cellulitis, necrotizing fasciitis and pyoderma. Eye infections encompass but are not limited to keratitis and conjunctivitis and ear infections encompass but are not limited to otitis externa.

The compositions described herein may be formulated for topical administration by including such dosage forms in an oil-in-water emulsion, or a water-in-oil emulsion. In such a formulation, the immediate release dosage form is in the continuous phase, and the delayed release dosage form is in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

The compositions described herein may be in the form of a liquid formulation. The liquid formulation may comprise a solution that includes a therapeutic agent dissolved in a solvent. Generally, any solvent that has the desired effect may be used in which the therapeutic agent dissolves and which can be administered to a subject. Generally, any concentration of therapeutic agent that has the desired effect can be used. The formulation in some variations is a solution which is unsaturated, a saturated or a supersaturated solution. The solvent may be a pure solvent or may be a mixture of liquid solvent components. In some variations the solution formed is an in situ gelling formulation. Solvents and types of solutions that may be used are well known to those versed in such drug delivery technologies.

Compositions of the invention may be administered topically. Therefore, contemplated for use herein are formulations adapted for the direct application to the skin. The composition may be in a form selected from the group comprising suspensions, emulsions, liquids, creams, oils, lotions, ointments, gels, hydrogels, pastes, plasters, roll-on liquids, skin patches, sprays, glass bead dressings, synthetic polymer dressings and solids. For instance, the compositions of the invention may be provided in the form of a water-based composition or ointment which is based on organic solvents such as oils. Alternatively, the compositions of the invention may be applied by way of a liquid spray comprising film forming components and at least a solvent in which the polyether ionophores are dispersed or solubilised. The administration of the polyether ionophores in accordance with the methods and compositions of the invention may be by any suitable means that results in an amount sufficient to treat a microbial infection on a subject's skin or to reduce microbial growth at the location of infection. The polyether ionophore may be contained in any appropriate amount and in any suitable carrier substance, and is generally present in an amount of 1-95% by weight of the total weight of the composition. The pharmaceutical or veterinary composition may be formulated according to the conventional pharmaceutical or veterinary practice (see, for example, Remington: The Science and Practice of Pharmacy, 20th edition, 2000, ed; A. R. Gennaro, Lippincott Williams & Wilkins, Philadelphia, and Encyclopedia of Pharmaceutical Technology, eds; J. Swarbrick and J. C. Boylan, 1988-1999, Marcel Dekker, New York; Remington's Pharmaceutical Sciences, 18$^{th}$ Edition, Mack Publishing Company, Easton, Pa., USA).

It is also within the scope of the invention to provide a medical device in the form of a patch or sponge, which includes polyether ionophore dosage forms having different release profiles, as hereinabove described.

The compositions of the invention may alternatively be formulated using nanotechnology drug delivery techniques such as those known in the art. Nanotechnology-based drug delivery systems have the advantage of improving bioavailability, patient compliance and reducing side effects.

The formulation of the composition of the invention includes the preparation of nanoparticles in the form of nanosuspensions or nanoemulsions, based on compound solubility. Nanosuspensions are dispersions of nanosized drug particles prepared by bottom-up or top-down technology and stabilised with suitable excipients. This approach may be applied to the polyether ionophores described herein where the polyether ioinophore has poor aqueous and lipid solubility in order to enhance saturation solubility and improve dissolution characteristics. Saturation solubility will be understood to be a compound-specific constant that depends on temperature, properties of the dissolution medium, and particle size (<1-2 μm).

The composition of the invention may be provided in the form of a nansuspension. For nanosuspensions, the increase in the surface area may lead to an increase in saturation solubility. Nanosuspensions are colloidal drug delivery systems, consisting of particles below 1 μm. Compositions of the invention may be in the form of nanosuspensions including nanocrystalline suspensions, solid lipid nanoparticles (SLNs), polymeric nanoparticles, nanocapsules, polymeric micelles and dendrimers. Nanosuspensions may be prepared using a top-down approach in that larger particles may be reduced to nanometre dimensions by a variety of techniques known in the art including wet-milling and high-pressure homogenisation. Alternatively, nanosuspensions may be prepared using a bottom-up technique in that controlled precipitation of particles may be carried out from solution.

The composition of the invention may be provided in the form of a nanoemulsion. Nanoemulsions are typically clear oil-in-water or water-in-oil biphasic systems, with a droplet size in the range of 100-500 nm, and with compounds of interest present in the hydrophobic phase. The preparation of nanoemulsions may improve the solubility of the polyether ionophores described herein, leading to better bioavailability. Nanosized suspensions may include agents for electrostatic or steric stabilisation such as polymers and surfactants. Compositions in the form of SLNs may comprise biodegradable lipids such as triglycerides, steroids, waxes and emulsifiers such as soybean lecithin, egg lecithin, and poloxamers. The preparation of a SLN preparation may involve dissolving/dispersing drug in melted lipid followed by hot or cold homogenisation. If hot homogenisation is used, the melted lipidic phase may be dispersed in an aqueous phase and an emulsion prepared. This may be solidified by cooling to achieve SLNs. If cold homogenisation is used, the lipidic phase may be solidified in liquid nitrogen and ground to micron size. The resulting powder may be subjected to high-pressure homogenisation in an aqueous surfactant solution.

Compositions of the invention may be in the form of a nanoemulsion. Polyether compounds as described herein may be dissolved in oils/liquid lipid and stabilised into an emulsion formulation. Nanoemulsions may be prepared using high- and low-energy droplet reduction techniques. High-energy methods may include high-pressure homogenisation, ultrasonication and microfluidisation. If the low-energy method is used, solvent diffusion and phase inversion will generate a spontaneous nanoemulsion. Lipids used in nanoemulsions may be selected from the group comprising triglycerides, soybean oil, safflower oil, and sesame oil. Other components such as emulsifiers, antioxidants, pH modifiers and preservatives may also be added.

The composition may be in the form of a controlled-release formulation may include a degradable or non-degradable polymer, hydrogel, organogel, or other physical construct that modifies the release of the polyether ionophore. It is understood that such formulations may include additional inactive ingredients that are added to provide desirable colour, stability, buffering capacity, dispersion, or other known desirable features. Such formulations may further include liposomes, such as emulsions, foams, micelles, insoluble monolayers, liquid crystals, phospholipid dispersions, lamellar layers and the like. Liposomes for use in the invention may be formed from standard vesicle-forming lipids, generally including neutral and negatively charged phospholipids and a sterol, such as cholesterol.

Compositions of the invention may be in the form of a solid dispersion.

Throughout this specification, unless the context requires otherwise, the word "comprise" or variations such as "comprises" or "comprising", will be understood to imply the inclusion of a stated integer or group of integers but not the exclusion of any other integer or group of integers.

EXAMPLE 1

Antibacterial Activity Against Isolates of *Staphylococcus*

Specific

As is apparent from the preceding summary of the invention, the invention relates to methods of treatment of microbial skin and skin structure infections in subjects such as humans, companion animals (for example canines), or livestock species (for example, bovine animals). As is also apparent from the preceding summary of the invention, the invention also relates to compositions used in such methods of treatment of topical microbial infections.

It will be understood that systemic exposure of a subject to be treated according to the methods of treatment of the invention, or the compositions described herein, is to be minimised in order to minimise toxic effects of exposure to therapeutically effective amounts of polyether ionophores. It will be appreciated that the cornified layer of the skin, the stratum corneum, functions as a physical barrier to absorption of therapeutically effective amounts of polyether ionophores, which compounds are prepared specifically in formulations to remain localised on the skin for localised antimicrobial activity and reduced toxic effects.

Materials and Methods

Bacterial Isolate Collection and Identification

Forty-two isolates of *Staphylococcus* of varying species and strain type were collected from isolate collections. Biochemical testing including coagulase, latex agglutination testing for protein A, Vogues-Proskauer tests and resistance to polymyxin B were used to identify the species of *Staphylococcus*. All isolates were also screened for resistance to various antimicrobials commonly used for the treatment of skin infections. This was performed using the disk diffusion method and resistance standards as outlined by the CLSI. The following antimicrobials were used: amoxicillin-clavulanic acid (30 µg), cephalothin (30 µg), clindamycin (2 µg), enrofloxacin (5 µg), erythromycin (15 µg), gentamicin (10 µg), imipenem (10 µg), oxacillin (1 µg), penicillin G (10 units), tetracycline (30 µg), 1:19 trimethoprim-sulfamethoxazole (25 µg) and vancomycin (30 µg). All strains resistant to oxacillin were found to also be resistant to amoxicillin-clavulanic acid, cephalothin and imipenem and these were determined to be methicillin-resistant strains. All isolate profiles are shown in FIG. 1.

Preparation of Antimicrobials

For each of the five test compounds, a 256 mg/mL stock solution was prepared by dissolving 2.56 grams of compound in 10 mL of dimethyl sulfoxide (DMSO). The resulting solution was then aliquoted into 500 µL volumes and stored at −80° C. until required. A 256 mg/mL stock solution of ampicillin was also prepared by dissolving 0.303 grams of ampicillin (Sigma A-0166) in 10 mL of DMSO. This solution was aliquoted and stored in the same manner as the five test compounds. When these compounds were required, a 256 µg/mL working solution was prepared by diluting 100 µL of stock solution (25.6 mg/mL) in 9.9 mL of cation adjusted Mueller Hinton Broth (CAMHB).

Minimum Inhibitory Concentration Assay

Minimum inhibitory concentration tests were performed according to CLSI Standards (CLSI 2012). 90 µL of one of the test compound solutions, or ampicillin, was added to the end column of a 96 well plate that contained 90 µL of CAMHB in each well. The solutions were then serially diluted across the row, leaving 2 columns for positive and negative controls (FIG. 2). A bacterial suspension was prepared by adding fresh colonies obtained from an overnight culture on Sheep Blood Agar (SBA) to a 9.1 g/L saline solution. This suspension was adjusted to a concentration of between $4\times10^8$ and $5\times10^8$ CFU/mL. Concentration of the suspension was determined by measuring optical density (OD) using a spectrophotometer at a wavelength of 600 nm where the correct concentration was determined to have an optical density of between 1.00 and 1.20. 1 mL of this suspension was added to 9 mL of saline before being added to all wells, excluding the negative control wells, in 10 µL volumes giving a final concentration of between $4\times10^5$ and $5\times10^5$ CFU/mL in each well. The tests were then incubated for 24 hours at 37° C. and then assessed both visually and using OD readings from a microplate reader at a wavelength of 600 nm. These tests were performed in duplicate but repeated if discrepancies were observed.

The minimum inhibitory concentration (MIC) was determined to be the lowest concentration of antibiotic that prevented growth of bacteria both visually and using OD readings. Direct statistical comparisons between the test compounds and ampicillin could not be performed in light of confidential information restrictions, such as restrictions on disclosure of information relating to the compound structure, such as molecular weight. Instead, MIC values were collated and used to determine the lowest concentration of each compound that was effective against 50% and 90% of isolates, referred to as the $MIC_{50}$ and $MIC_{90}$ respectively. These values as well as the range of MIC values were then used for direct comparisons between test compounds and for general comparisons with ampicillin.

Minimum Bactericidal Concentration Determination

Figure 3:
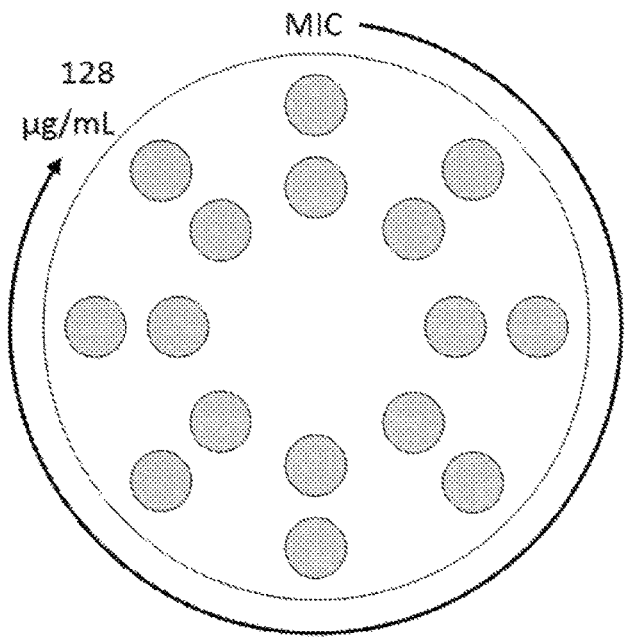
FIG. 3 is a diagrammatic representation of the Minimum Bactericidal Concentration test with shaded areas representing the placement of 10 μL volumes in duplicate and the direction of the arrow represents the increasing concentration as read clockwise around the plate according to Example 1.

Following determination of the MIC using the 96 well MIC plate, a variation of the drop plate method was used to determine minimum bactericidal concentration (MBC) for each of the test compounds. These were analysed using samples taken from the MIC plate following incubation. For each compound, a 10 µL drop of each concentration equal to or higher than the MIC was pipetted onto Sheep Blood Agar in a clockwise manner (FIG. 3). Each concentration was pipetted in duplicate with duplicates being pipetted on an inner ring of drops. The plates were incubated at 37° C. overnight and assessed the following day for growth. The MBC was defined as the concentration at which 99.9% of colonies were eradicated, which was visually assessed by a lack of growth on the agar where the drop was placed. Using these data, bactericidal activity could be suggested for some of the compounds. The MBC values for 50% and 90% of the isolates (MBC50 and MBC90) were calculated and assessed along with the MBC range in order to select compounds for further study.

Time-Kill Kinetics Assay

Following assessment of MIC and MBC results, two compounds were chosen for analysis using microdilution time-kill assays, LP 1369 and LP 6315 and these were compared to ampicillin. Time-kill assays were performed according to the M26-A guidelines of the CLSI, with modifications. The test compounds and ampicillin were serial diluted in CAMHB across the rows of a 96 well plate and a bacterial suspension was prepared and added in the same manner as the MIC testing. The 96 well plates were then incubated at 37° C. for 48 hours being removed at specific time points and OD for the positive control wells as well as one, four and eight times the MIC of the compound specific to the strain being tested were assessed using a spectrophotometer at a wavelength of 600 nm. The time points assessed were 0, 1, 2, 4, 8, 12, 24 and 48 hours after the addition of the bacterial suspension to the wells. Each test compound was tested in triplicate while ampicillin was tested in duplicate and this test was independently repeated. The bacterial strains used for the microdilution assays were chosen based on bactericidal activity evident during MBC testing. One strain from each of the categories of *Staphylococcus* in the isolate collection (methicillin-sensitive, methicillin resistant and coagulase negative) were selected as well as the ATCC reference strain for comparison. These strains were strains MSS 1, MSS 11, MRSA 9 and the ATCC 49775 reference strain.

Due to the detection limit of the OD measurements, the time-kill assays were also performed in macrodilution. In 15 mL tubes, 9 mL volumes of the test compounds in CAMHB were prepared at one, four and eight times the MIC concentration and 9 mL volumes of ampicillin were prepared in CAMHB at one and four times the MIC. 1 mL of a 4 to $5\times10^6$ bacterial suspension (as prepared for MIC testing) was added to each of the tubes as well as a growth control tube containing only 9 mL of CAMHB. These tubes were incubated at 37° C. in an orbital shaker rotating at 100 rpm for 24 hours. At 0, 1, 4, 8, 12 and 24 hours after addition of the bacteria, 100 µL samples were removed from each tube and serial diluted in 9.1 g/L saline solution. The dilutions were then plated in duplicate onto plate count agar and incubated for 24 hours at 37° C. After incubation, viable counts were obtained from the number of colonies visible on the agar and these were used to calculate the number of CFU/mL at each time point. For the macrodilution time-kill analysis, only the ATCC 49775 reference strain and MRSA 9 were assessed in order to further investigate the antibacterial activity against methicillin-resistant strains. These macrodilution time-kill assays were independently repeated and bactericidal activity was defined as a ≥3 log decrease in the number of CFU/mL.

Eukaryotic Cell Toxicity Testing

Erythrocyte haemolysis was used in order to test the toxicity of all five compounds to eukaryotic cells. Blood samples were washed using 9.1 g/L saline solution and centrifuged at 2500 rpm for 10 minutes. This process was repeated until cellular debris and partially lysed cells were removed from solution. 2 mL of the remaining blood cells were suspended in 98 mL of 9.1 g/L saline solution to produce a 2% blood cell solution, which was dispensed in 90 µL volumes into the wells of a 96 well plate. The compound solutions as well as chloramphenicol were prepared from stock solution to a concentration of 256 µg/mL (as described above). Chloramphenicol was used as a negative control for erythrocyte lysis while a ready to use solution of amphotericin B was used as a positive control. 90 µL of the compounds and controls were added to the final well in different rows. These compounds were serially diluted across the row in order to test the different concentrations of antimicrobials. Wells containing only 2% blood solution were also used to assess variation between readings from different columns on the 96 well plates. These tests were incubated at 37° C. for one hour and then assessed for lysis both visually and using a microplate reader to measure optical density at 600 nm wavelengths. Each test was performed in duplicate and then repeated in quadruplicate in order to ensure accuracy.

Results

Figure 4:
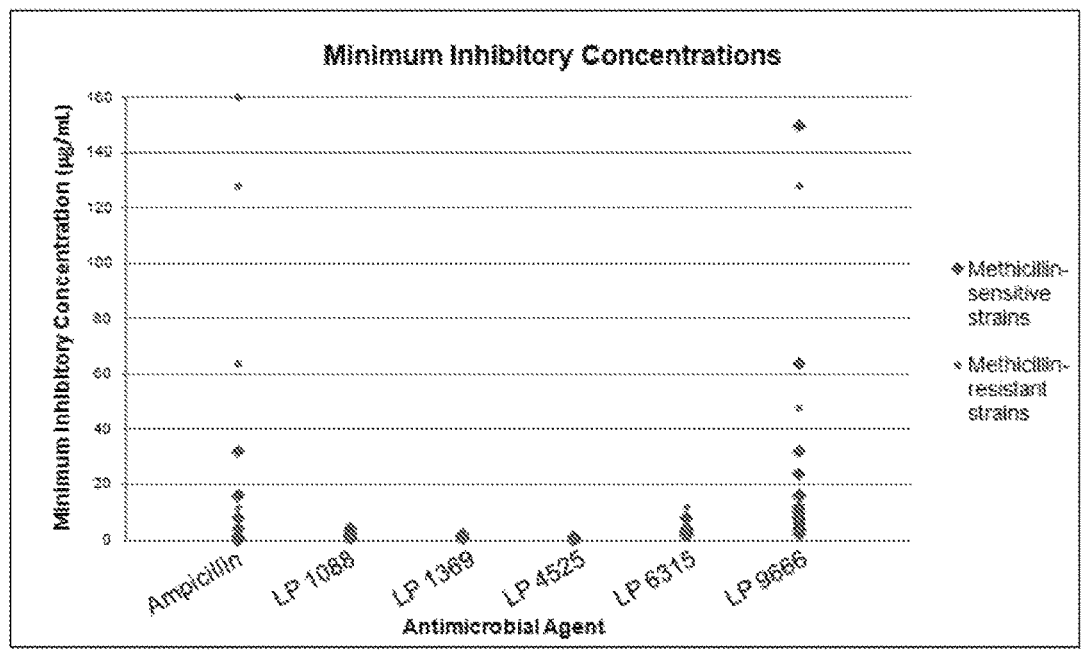
FIG. 4 shows a graph of the Minimum Inhibitory Concentrations for the individual isolates separated into methicillin-sensitive and methicillin-resistant strains; values shown as higher than 128 μg/mL represent strains where no MIC value was obtained within the range of concentrations tested (0.25-128 μg/mL) according to Example 1.

MIC testing results confirmed antibacterial activity for all test compounds in both methicillin sensitive and methicillin-resistant staphylococci. All test compounds had constantly low MIC values (below or equal to 16 µg/mL) for all strains with the exception of compound LP 9666 as shown in FIG. 4. MIC variation was demonstrated for compound LP 9666 as indicated by the high $MIC_{90}$ value and broad MIC range. While the range of MIC values was similar to that of ampicillin, there was no distinction between methicillin-resistant and methicillin-sensitive strains similar to that observed in the MIC values for ampicillin. The $MIC_{50}$, $MIC_{90}$ and MIC ranges for methicillin-sensitive *Staphylococcus* strains are shown in FIG. 5. The $MIC_{50}$ values for most of the test compounds except for LP 9666 were comparable to ampicillin while the $MIC_{90}$ values were considerably lower. This was reflected in the ranges for the test compounds across the strain collection which showed smaller ranges than ampicillin for all the test compounds except LP 9666. A similar trend was observed for methicillin-resistant isolates as shown in FIG. 6. Compounds LP 1088, 1369, 4525 and 6315 demonstrated $MIC_{50}$ and $MIC_{90}$ values considerably lower than ampicillin as well as narrow MIC ranges. However, while LP 9666 had higher MIC50 and MIC90 values than the other four test compounds, they were considerably lower than ampicillin for the methicillin-resistant strains.

All five test compounds exhibited bactericidal activity in high concentrations but compounds LP 1088, 1369, 4525 and 6315 also showed some bactericidal activity in lower concentrations. Compounds LP 1088 and 1369 exhibited bactericidal activity more consistently for methicillin-sensitive strains while compounds LP 4525 and 6315 exhibited bactericidal activity more consistently for methicillin-sensitive strains, as shown in FIG. 7.

Figures 7, 8:
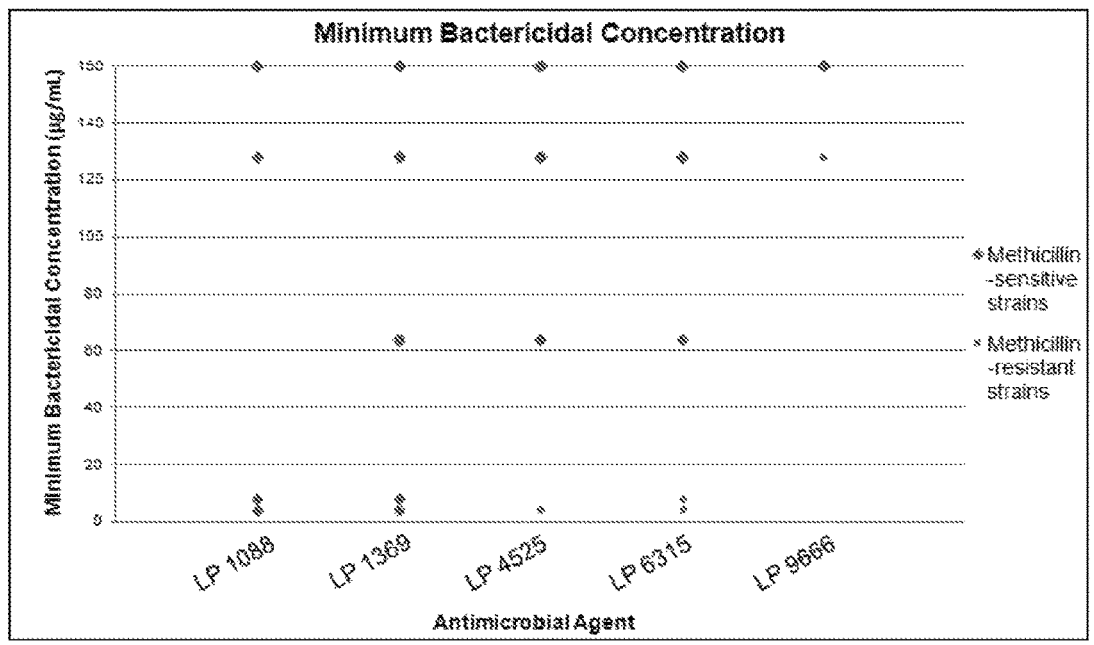
FIG. 7 shows a graph of the minimum bactericidal concentrations for individual isolates separated into methicillin-sensitive and methicillin-resistant strains; values shown as higher than 128 μg/mL represent strains where no MBC value was obtained within the range of concentrations tested (0.25-128 μg/mL) according to Example 1.
FIG. 8 shows a table showing the $MBC_{50}$, $MBC_{90}$ and MBC ranges for the methicillin-sensitive isolates for the five test compounds according to Example 1.
Figures 9, 10:
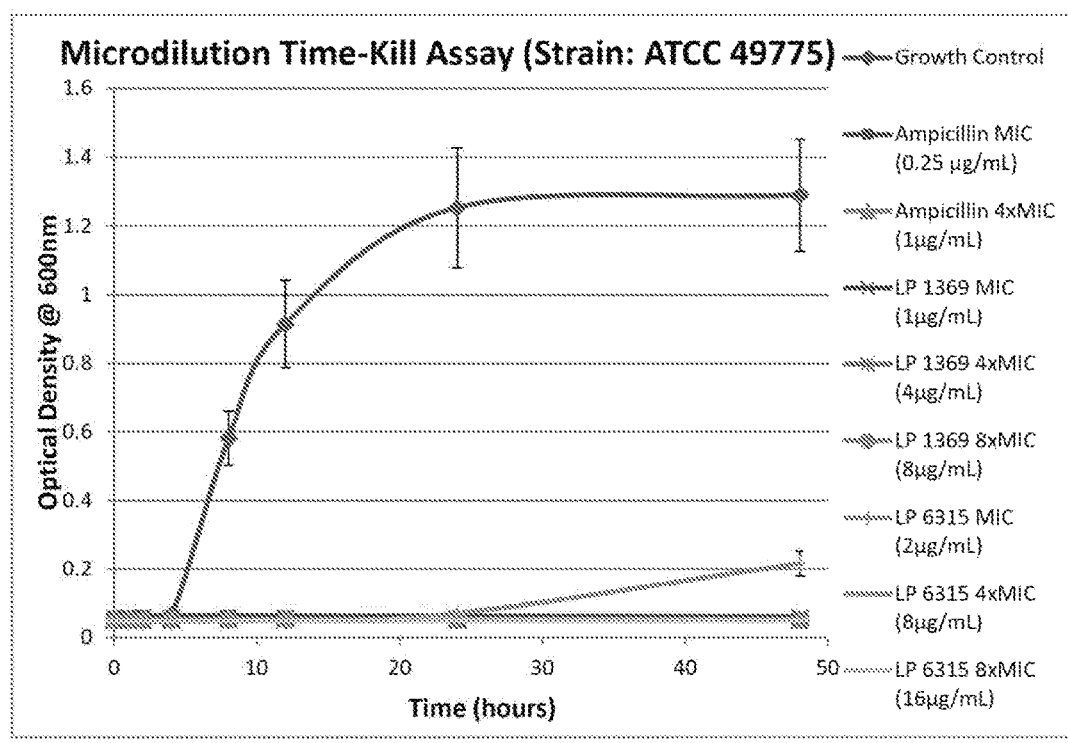
FIG. 9 shows a table illustrating the $MBC_{50}$, $MBC_{90}$ and MBC ranges for the methicillin-resistant isolates for the five test compounds according to Example 1.
FIG. 10 shows a graph illustrating the optical density measurements obtained for the microdilution time-kill assay of ATCC 49775 over 48 hours using various concentrations of ampicillin, LP 1369 and LP 6315 compared to a growth curve according to Example 1.

Comparison of the $MBC_{50}$, $MBC_{90}$ and MBC ranges for the five test compounds for methicillin-sensitive and methicillin-resistant strains are shown in FIGS. 8 and 9, respectively. The $MBC_{50}$ and $MBC_{90}$ values showed that while some strain-dependent bactericidal activity was evident for the test compounds at low concentrations, most compounds were bacteriostatic for the majority of the strains tested. The greatest bactericidal activity was observed for compounds LP 1369 against methicillin-sensitive isolates and LP6315 for methicillin-resistant isolates as these demonstrated the lowest $MBC_{50}$ values despite their similar MBC ranges.

Figure 11:
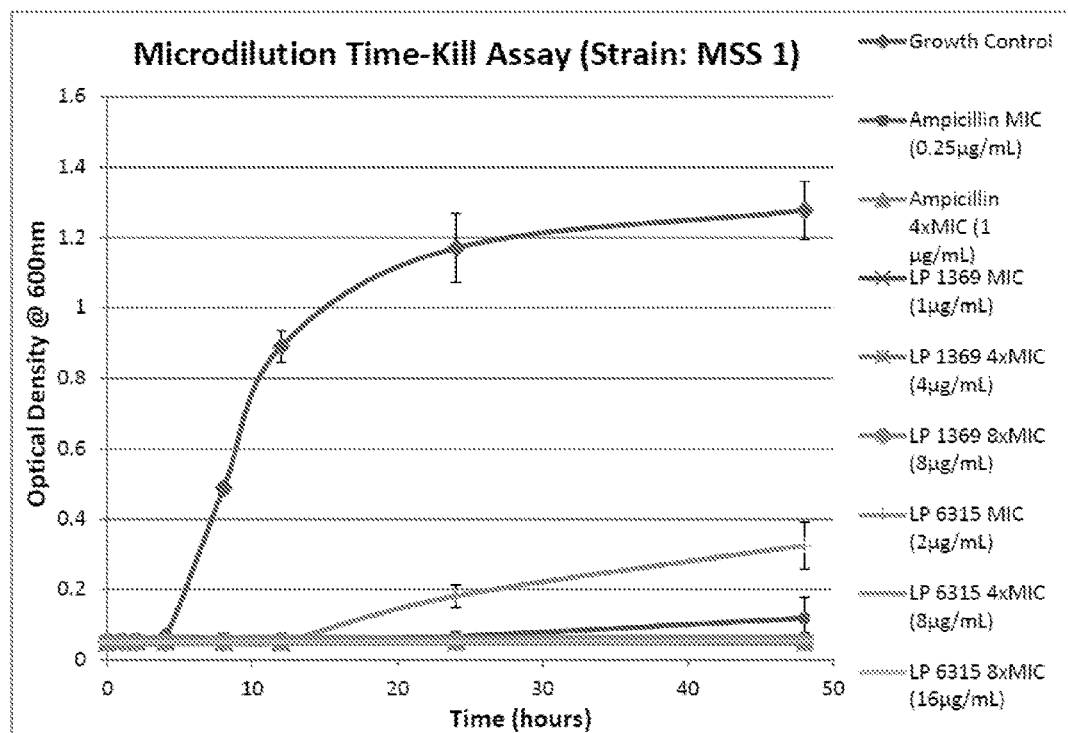
FIG. 11 shows a graph illustrating the optical density measurements obtained for the microdilution time-kill assay of MSS 1 over 48 hours using various concentrations of ampicillin, LP 1369 and LP 6315 compared to a growth curve according to Example 1.
Figure 12:
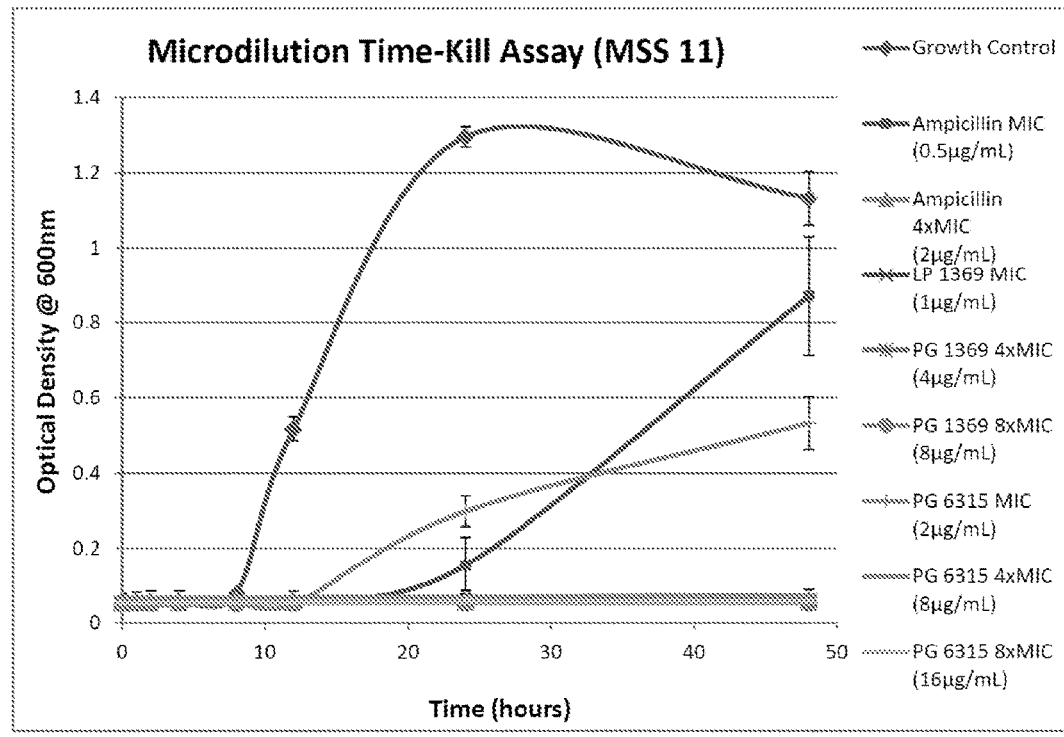
FIG. 12 shows a graph illustrating the optical density measurements obtained for microdilution time-kill assay of MSS 11 over 48 hours using various concentrations of ampicillin, LP 1369 and LP 6315 compared to a growth curve according to Example 1.
Figure 13:
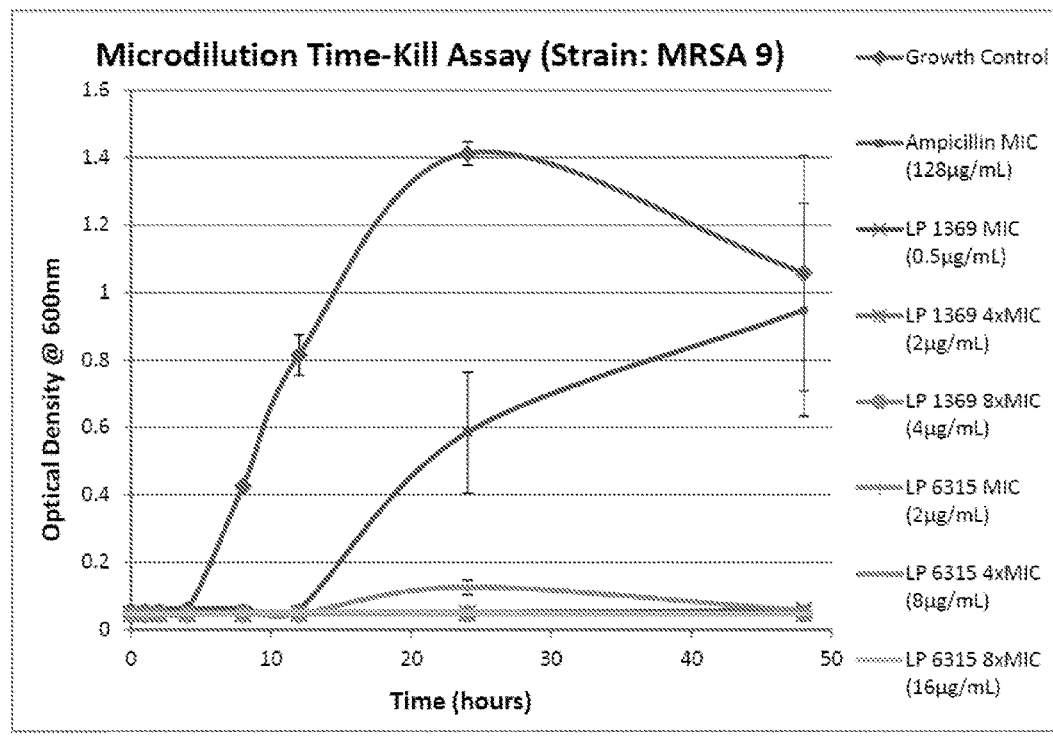
FIG. 13 shows a graph illustrating the optical density measurements obtained for microdilution time-kill assay of MRSA over 48 hours using various concentrations of ampicillin, LP 1369 and LP 6315 compared to a growth curve according to Example 1.

In the microdilution time-kill assay, both compounds LP 1369 and LP 6315 prevented the growth of the ATCC reference strain over a 48 hour period compared to the growth control (FIG. 10). Some growth was observed after 48 hours for LP 6315 at the MIC but this was still significantly less than that of the growth control. Similar trends were observed for the kill kinetics assays performed for methicillin-sensitive strains MSS 1 and MSS 11 (FIGS. 11 and 12, respectively). Like the ATCC reference strain, all the compounds prevented the growth of bacteria to the levels of the growth control and, for most concentrations, prevented growth above the initial concentration. However, as with the ATCC strain, growth was observed at the MIC of LP 6315 but was observed 24 hours sooner and continued to increase for the final 24 hours. A similar trend was also observed in the MIC for ampicillin for MSS 11 but the increase in the number of bacteria in the final 24 hours was much steeper than that of the 1×MIC kill kinetics assay for LP 6315. For the time-kill assay for MRSA 9 (FIG. 13), an increase in the number of bacteria after 12 hours was evident for ampicillin and the resulting growth after 48 hours was comparable to the growth control. However, while an increase for 1×MIC of LP 6315 was evident after 24 hours, after 48 hours this growth was no longer observed.

Figure 14:
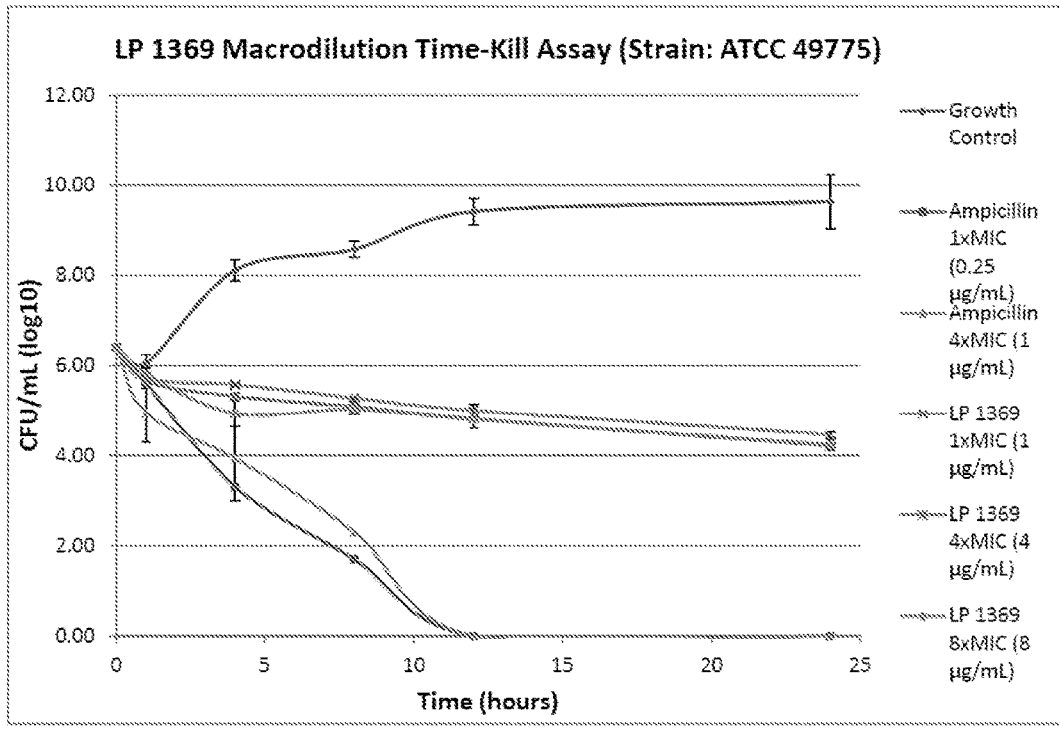
FIG. 14 shows a graph illustrating the number of viable colonies (log10) of ATCC 49775 over 24 hours compared to introduction to one, four and eight times the MIC of LP 1369, one and four times the MIC of ampicillin according to Example 1.
Figures 15, 16:
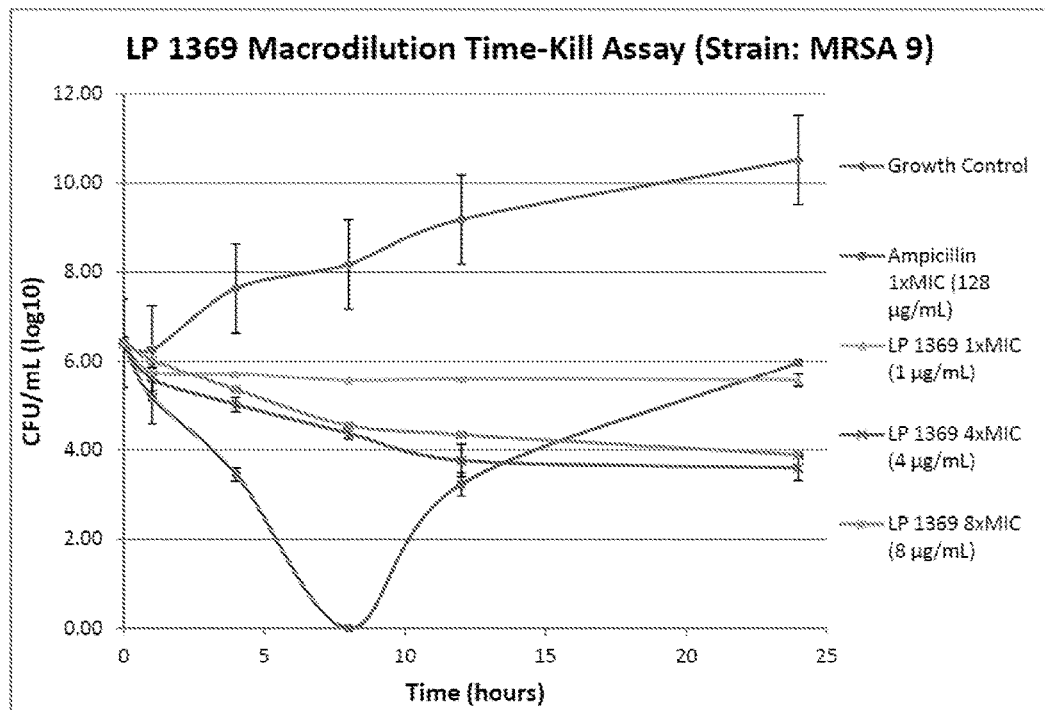
FIG. 15 shows a graph illustrating the number of viable colonies (log10) of MRSA 9 over 24 hours compared to introduction to one, four and eight times the MIC of LP 1369, one and four times the MIC of ampicillin according to Example 1.
FIG. 16 shows a table setting out the change in number of CFU/mL (log10) for ATCC 49775 and MRSA 9 over 24 hours in various concentrations of ampicillin or LP 1369 compared to a growth control according to Example 1.

Further time-kill assays in macrodilution showed a relatively constant decrease in the number of viable bacteria over the initial 24 hour period for both test compounds regardless of strain. FIGS. 14 and 15 show that the effect of compound LP 1369 on the number of bacteria was significant compared to the growth control for all the concentrations tested, but that this compound exhibited higher potency at four times the MIC than at eight times the concentration for both MRSA 9 and the ATCC 49775 reference strain. Total reduction in the number of bacteria was assessed, as shown in FIG. 16. As expected, ampicillin was shown to be bactericidal for both strains as the decrease in the number of viable bacteria was >3-$log_{10}$ reduction while compound LP 1369 was found to be bacteriostatic for all concentrations as the decrease in the number of viable bacteria was <3-$log_{10}$ reduction.

Figure 17:
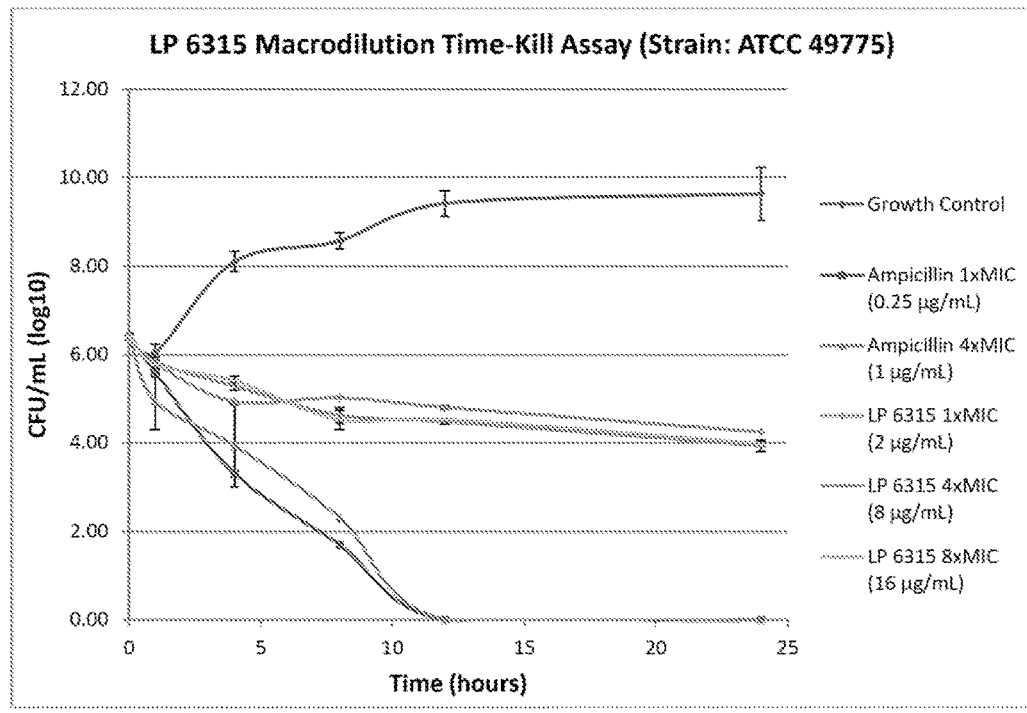
FIG. 17 shows a graph illustrating the number of viable colonies (log10) of ATCC 49775 over 24 hours compared to introduction to one, four and eight times the MIC of LP 6315, one and four times the MIC of ampicillin according to Example 1.
Figure 18:
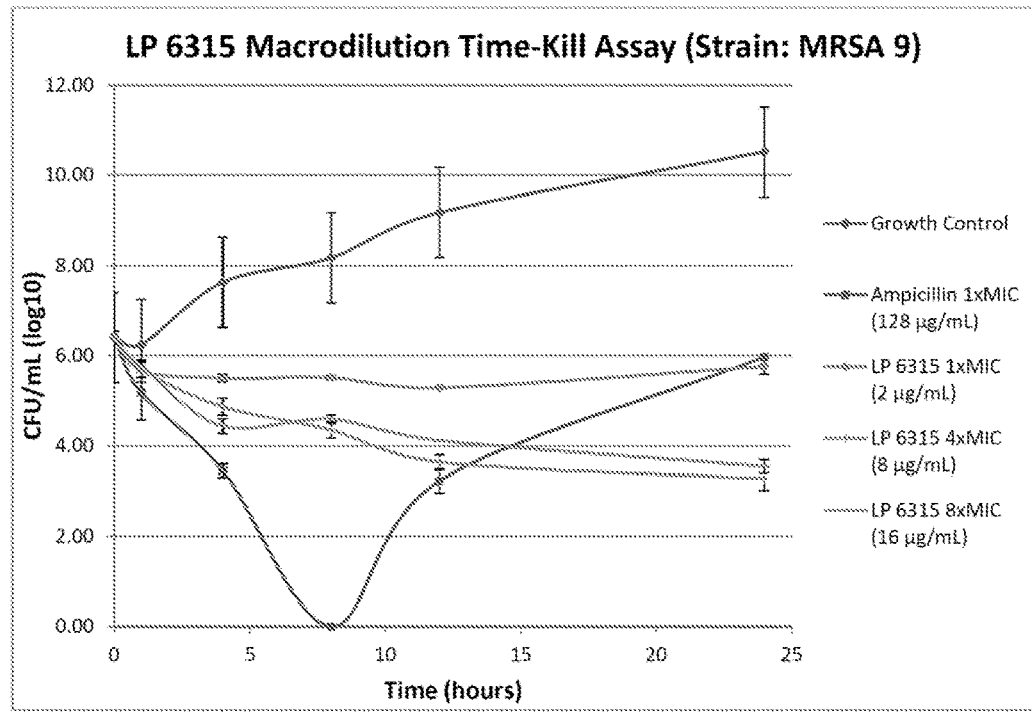
FIG. 18 shows a graph illustrating the number of viable colonies (log10) of MRSA 9 over 24 hours compared to introduction to one, four and eight times the MIC of LP 6315, one and four times the MIC of ampicillin according to Example 1.

A similar trend to LP 1369 was observed in LP 6315. For the ATCC reference strain (FIG. 17), there was a constant decrease in the number of bacteria over the 24 hour period for all three concentrations of the test compound. For MRSA 9, shown in FIG. 18, all concentrations decreased the number of bacteria for the first 12 hours but an increase was observed between 12 and 24 hours for the MIC. When these reductions were quantified (FIG. 19), ampicillin was shown to be bactericidal as expected while most concentrations of LP 6315 were shown to be bacteriostatic. However, at four times the MIC, LP 6315 was observed to be bactericidal against MRSA as the decrease in colonies was >3–$log_{10}$.

Figures 19, 20:
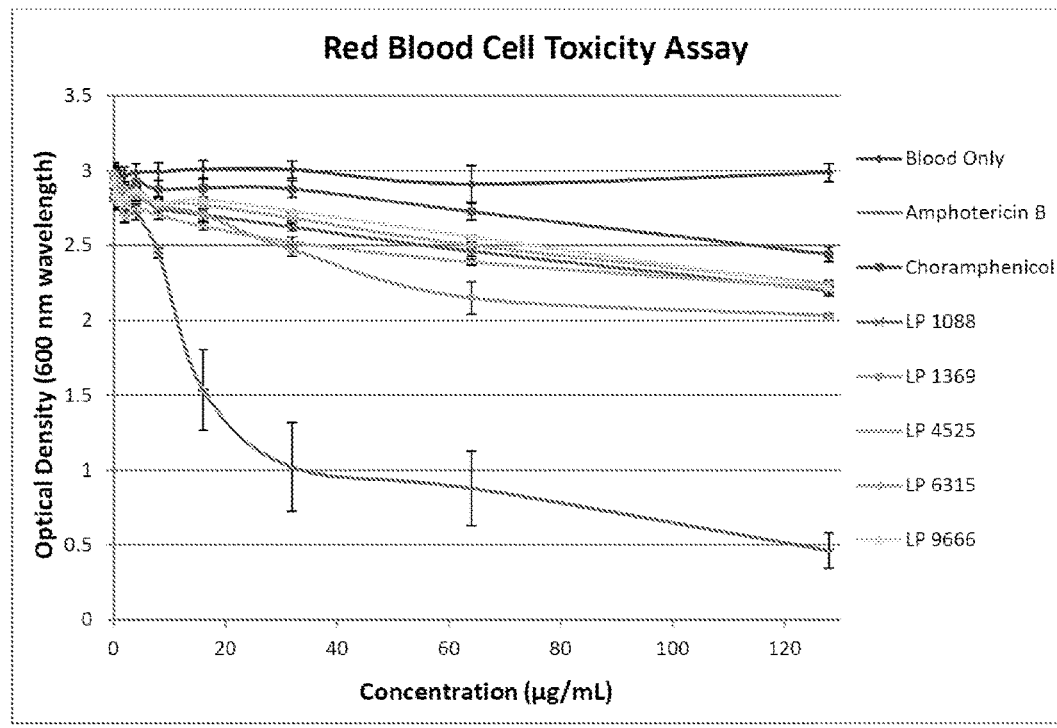
FIG. 19 shows a table illustrating the change in number of CFU/mL (log10) for ATCC 49775 and MRSA 9 over 24 hours in various concentrations of ampicillin or LP 6315 compared to a growth control according to Example 1.
FIG. 20 shows a graph illustrating the optical density readings obtained for the red blood cell toxicity assay for each test compound at various concentrations as well as positive and negative controls and blood only readings according to Example 1.

The optical density readings from the eukaryotic toxicity assays are shown below in FIG. 20. A decrease in optical density was interpreted as indicative of lysis of the red blood cells. While there was a decrease in optical density for all test compounds in concentrations of 32 μg/mL and higher, for all of the compounds except LP 1369, this decrease was not significant as the decrease was comparable to that of chloramphenicol and as no lysis of red blood cells was visually observed at these concentrations. While the level of lysis was not as high as amphotericin B for compound LP 1369, some lysis of cells was observed within the concentration range 32-128 μg/mL but this was most visually evident at 64 μg/mL.

EXAMPLE 2

Antibacterial Activity Against Skin Lesion Isolates

Isolates of *Staphylococcus pseudintermedius* were collected from skin lesions of various breeds of dogs. The presence of mec gene and the resistance profile were determined according to the materials and methods described in example 1.

FIG. 21 shows the results obtained for RT-PCR determination of mecA gene presence and resistance profile to various antibiotics. FIGS. 22A-22B show the resistance profile of all the isolates obtained. FIG. 23 shows the results of testing ampicillin LP1369, LP4525 and LP6315 against each isolate as well as providing a summary of the MIC50, MIC90, MIC mode and MIC range.

EXAMPLE 3

Antibacterial Activity Against Bovine Mastitis Isolates

Summary

Five antimicrobial agents, LP 1088, LP 1369, LP 4525, LP 6315 and LP 9666, were tested against 51 Australian bovine mastitis isolates, primarily pathogenic *S. aureus* species, *S. agalactiae* and *S. uberis*. LP4525 exhibited the lowest $MIC_{50}$ and $MIC_{90}$ (0.25 μg/ml and 1 μg/ml respectively). For LP1088, LP1369, LP6315 and LP9666, an $MIC_{90}$ of 2 µg/ml, 4 µg/ml, 4 µg/ml and 128 µg/ml was obtained, respectively. All tested antimicrobials elicited MBC values that suggested that these compounds are bacteriostatic against mastitis pathogens. LP4525 appears to be the most promising candidate intramammary antimicrobial agent to treat bovine mastitis cases resulting from infection with Gram-positive bacteria.

Materials and Methods

Bacterial Isolate Collection and Identification

Fifty-one dairy bovine mastitis isolates, encompassing a variety of bacterial species, were isolated from milk samples collected from dairy farms in rural South Australia by the University of Adelaide Ambulatory Clinic. Cellular morphology observed from Gram stains and catalase testing was used to differentiate *Staphylococcus, Streptococcus* and *Corynebacterium* species from Gram-negative species. Further biochemical testing including coagulase, Lancefield grouping, esculin hydrolysis and CAMP tests were used to identify the isolates to species level. Where biochemical test results were not definitive in identifying species, amplification and sequencing of the 16S ribosomal RNA gene was used to confirm the identity of the isolates.

Preparation of Antimicrobials

For each of the five test compounds, a 256 mg/ml stock solution was created by dissolving 2.56 grams of compound in 10 ml of dimethyl sulfoxide (DMSO). The resulting solution was then aliquoted into 500 µL volumes and stored at −80° C. A 256 mg/ml stock solution of ampicillin was also created by dissolving 0.303 grams of ampicillin (Sigma A-0166) in 10 ml of DMSO. This solution was aliquoted and stored in the same manner as the five test compounds. When these compounds were required, a 256 µg/ml working solution was created by diluting 100 µl of stock solution (25.6 mg/ml) in 9.9 ml of Cation-Adjusted Mueller Hinton Broth (CAMHB)

Minimum Inhibitory Concentration Assay

Minimum inhibitory concentration tests were performed in the manner outlined by the CLSI (CLSI 2012). Test compounds were dispensed into a 96-well microtitre tray containing 90 µl of CAMHB in 90 µl volumes and serial diluted to obtain a concentration gradient ranging from 128 µg/ml to 0.25 µg/ml (see FIG. 24). For *Streptococcus* species, CAMHB was replaced with a CAMHB supplement with 4% lysed-sheep blood (4% LSB:CAMHB). 4% LSB:CAMHB was prepared by mixing 5 ml sheep blood to 5 ml milliQ water, and repeated freezing at −20° C. and thawing, followed by centrifuged for 20 min at 7000 rpm. 7 ml of the supernatant was removed and added to 93 mL of CAMB.

Bacterial suspensions were prepared by emulsifying fresh colonies obtained from an overnight culture on Sheep Blood Agar (SBA) in 4 mls of 9.1 g/l physiological saline to an optical density read at 600 nm ($OD_{600}$ nm) between 1.00 and 1.20. Standardised bacterial suspensions were diluted 1:10 in physiological saline and dispensed into all wells, excluding the negative control wells, in 10 µL volumes giving a final concentration of between $4 \times 10^5$ and $5 \times 10^5$ CFU/mL in each well. 96-well microtitre trays were incubated for 24 hours at 37° C. in 5% $CO_2$ and then assessed both visually and using OD readings from a microplate reader at a wavelength of 600 nm. These tests were performed in duplicate and repeated if discrepancies in MIC values were observed between replicates.

The minimum inhibitory concentration (MIC) was determined to be the lowest concentration of antibiotic that prevented growth of bacteria both visually and using OD readings. MIC values were collated and used to determine the lowest concentration of each compound effective against 50% and 90% of isolates, known as the $MIC_{50}$ and $MIC_{90}$ respectively. These values as well as the range of MIC values were then used for direct comparisons between test compounds and for general comparisons with ampicillin.

Minimum Bactericidal Concentration Determination

Following MIC determination, a variation of the drop plate method was used to determine the minimum bactericidal concentration (MBC) for each of the test compound. MBCs were determined by aliquotting a 10 µL drop of each concentration from the microtitre plate onto SBA, which were then incubated for 16 hrs at 37° C. The MBC was defined as the concentration at which 99.9% of colonies were eradicated, which was visually assessed by a lack of growth on the agar where the drop was placed. The MBC values for 50% and 90% of the isolates ($MBC_{50}$ and $MBC_{90}$) were calculated and assessed along with the MBC range in order to select compounds for further study.

Results

Figures 24, 25, 26:
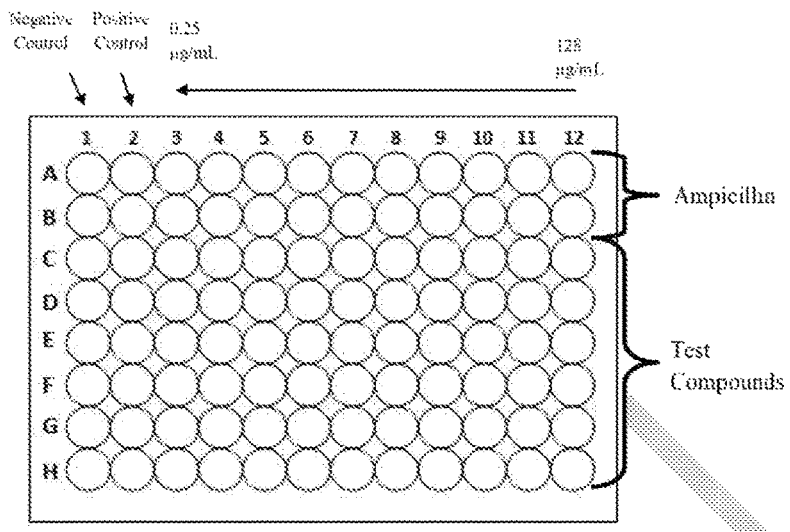
FIG. 24 is a diagrammatic representation showing the 96 well microtitre tray layout for Minimum Inhibitory Concentration Testing according to Example 3.
FIG. 25 is a table showing the $MIC_{50}$, $MIC_{90}$, MIC range and $MBC_{50}$, $MBC_{90}$, and MBC range of each compound tested according to Example 3.
FIG. 26 is a table showing the $MIC_{50}$, $MIC_{90}$, MIC range and $MBC_{50}$, $MBC_{90}$, and MBC range of each compound tested against 14 *Staphylococcus aureus* isolates according to Example 3.

Antibacterial activity against the bovine mastitis isolates was observed for all five of the test compounds, LP1088, LP1369, LP4525, LP6315 and LP9666. LP4525 demonstrated the lowest MIC90 (1 µg/ml). The values for LP1088, LP1369 and LP6315 were one to two dilutions higher, whereas the value for LP9666 was several dilutions higher (FIG. 25). In contrast to the low $MIC_{90}$ values obtained for 4 of the 5 compounds, the across the board high $MBC_{90}$ values indicate that all compounds appear for the most part to be bacteriostatic, although bactericidal activity at quite low concentrations above the MIC (2-8 µg/ml) was observed for some isolates. For the MICs and MBCs of individual isolates for all five compounds refer to FIG. 31 and FIG. 32.

When the MIC and MBC data was analysed according to the species of the isolates, it was evident that the $MIC_{50}$ and $MIC_{90}$ values were lower for Streptococcus species in comparison to the *Staphylococcus* species (FIGS. 26 to 30A-30B). However, the MIC ranges indicate that the differences between the two groups of pathogens are not significant. The MBC data was also highly variable within species, with some staphylococci and streptococci strains effectively killed at concentrations only just above the MIC (eg. for LP4525 and LP6315), but no significant difference was identified between species.

The preliminary results from this study suggest that all five compounds exhibit bacteriostatic activity with some compounds exhibiting strain-dependent bactericidal activity at high concentrations. Although all compounds exhibited some turbidity upon dilution in Cation Adjusted Mueller Hinton Broth, LP1088, LP1369, LP4525 and LP6315 all exhibited low MIC values. LP9666, however, had significantly higher $MIC_{90}$ values for each of the groups of mastitis pathogens, and this may be due to the large amount of precipitate formed when diluted in Cation Adjusted Mueller Hinton Broth. LP4525 had the most consistent MIC values for all isolates, and this is evidenced by the small MIC range. LP4525 also has a lower $MIC_{90}$ value compared to all compounds. We also found that one Gram-negative bacterial isolate (isolate 2825) in the collection was susceptible to all five compounds.

EXAMPLE 4

Preparation of a Topical Formulation for the Study Presented in Example 5

Ointment Formulation

The following formulation was prepared for the skin application of LP1369 in the murine studies presented in Example 5.

| | |
|---|---|
| Paraffin oil | 49.0 g |
| Vaseline | 49.0 g |
| LP1369 | 2.0 g |

LP1369 and paraffin oil were mixed and added to a ball mill (model Micro Mill Pulverisette 7 Premium Line, Fritsch Co., Rhineland-Palatinate, Germany) and wet milled at 1000 rpm for 10 cycles, with a duration of 3 minutes per cycle for a milling time of 0.5 hour. After milling, drug particle size was measured to be 1-6 µm. The suspension attained was separated from the milling beads using a disposable plastic pipette. The Vaseline was heated at 100° C. until the Vaseline melted and then cooled (by room temperature) until it dropped to 50° C. The LP 1369/paraffin oil suspension was dripped into the Vaseline and the composition homogenized at 50° C. until it formed a uniform ointment.

Other potential formulations embodied by the present invention include:

| Ointment formulation | |
|---|---|
| Lanolin | 10.0 g |
| Vaseline | 80.0 g |
| Parafin oil | 7.9 g |
| Preservative | 0.1 g |
| LP 1369 (2%) | 2.0 g |
| Gel Formulations | |
| PEG 4000 | 35.0 g |
| PEG 200 | 40.0 g |
| Glycerol | 6.0 g |
| Distilled water | 17.0 g |
| LP1369 | 2.0 g |
| Cream Formulation | |
| Glycerol monostearate | 12.0 g |
| Vaseline | 15.0 g |
| Stearate acid | 1.3 g |
| Paraffin oil | 5.0 g |
| Potassium stearate | 0.7 g |
| Glycerol | 10.0 g |
| Preservative | 0.1 g |
| LP 1369 (2%) | 2.0 g |
| Distilled water | to 100 g |

EXAMPLE 5

Efficacy of Investigational Veterinary Products Containing LP1369 in the Treatment of a Skin Condition in Mice Summary of the Model: A useful animal model system should be clinically relevant, experimentally robust, ethically acceptable, convenient to perform and should provide reliable and reproducible results. There are many animal models of topical skin infection that have been described including the croton oil-inflamed skin model (Akiyama, H., H. Kanzaki, Y. Abe, J. Tada and J. Arata (1994). "Staphylococcus aureus infection on experimental croton oil-inflamed skin in mice." Journal of Dermatological Science 8(1): 1-10), the burnt skin model (Stieritz, D. D., A. Bondi, D. McDermott and E. B. Michaels (1982). "A burned mouse model to evaluate anti-pseudomonas activity of topical agents." Journal of Antimicrobial Chemotherapy 9(2): 133-140), the skin suture-wound model (McRipley, R. J. and R. R. Whitney (1976). "Characterization and Quantitation of Experimental Surgical-Wound Infections Used to Evaluate Topical Antibacterial Agents." Antimicrobial Agents and Chemotherapy 10(1): 38-44), the skin tape-stripping model (Kugelberg, E., T. Norstrom, T. K. Petersen, T. Duvold, D. I. Andersson and D. Hughes (2005). "Establishment of a Superficial Skin Infection Model in Mice by Using *Staphylococcus aureus* and *Streptococcus pyogenes*." Antimicrobial Agents and Chemotherapy 49(8): 3435-3441) and the linear full thickness scalpel cut method (Guo, Y., R. I. Ramos, J. S. Cho, N. P. Donegan, A. L. Cheung and L. S. Miller (2013). "In Vivo Bioluminescence Imaging To Evaluate Systemic and Topical Antibiotics against Community-Acquired Methicillin-Resistant *Staphylococcus aureus*-Infected Skin Wounds in Mice." Antimicrobial Agents and Chemotherapy 57(2): 855-863).

Preliminary studies prior to the conduct to the current study established a new method of skin infection arising from a detailed study of the models mentioned above. Briefly, study mice are anaesthetised, a patch of dorsal skin is clipped to reveal the skin and a circular area of skin is removed with a hand held punch, leaving a wound on the dorsum with a central cavity. The wound is infected with a known number of the challenge organism. Approximately four to six hours after infection, the wound is either treated topically with a vehicle formulation or an active formulation. The infected skin wound is retreated every 12 hours for a total of 11 treatments. Mice are humanely euthanased, the area of the original infected wound is dissected and removed and its bacterial content quantified by standard microbiologic tests. In this way, the change in bacterial concentration due to treatment with the active formulation can be readily determined by examining the reduction in bacterial burden compared with the vehicle control.

Materials and Methods

Preparation of Infection Inoculum

Fresh cultures of bacteria were grown on Sheep Blood Agar at 37° C. for 16-18 hours. A few typical colonies were selected and suspended in 10 ml of Tryptic Soy Broth and incubated overnight in a shaking incubator (240 rpm) at 37° C. The overnight suspension was vortexed and diluted (1:100) in fresh Tryptic soy broth (100 µl [0.1 ml] in 9.9 ml broth). The fresh suspension was incubated for 3 hours in a shaking incubator (as above) in order to obtain mid-logarithmic phase bacteria. Bacteria were pelleted through centrifugation at 7,500 rpm for 10 mins. Broth supernatant was removed and bacteria suspended in 10 ml Phosphate Buffered Saline (PBS). These steps were repeated a further two times. The density of the suspension was checked by measuring absorbance at 600 nm, using a spectrophotometer with saline as a blank, to confirm the target density at a reading of approximately 0.100, consistent with a bacterial density of $2.5 \times 10^8$ CFU/ml. The suspension was placed into a rack placed into a lockable transport box with an ice brick to maintain refrigeration during transport, followed by storage in cool room upon arrival at the mouse skin infection laboratory. Final suspension was mixed thoroughly before inoculating the skin wounds created in mice.

In order to ensure the purity and accuracy of the suspension, the following steps were performed prior to placement into lock box.

Purity of bacterial suspension ensured by spreading 100 µl of the final suspension onto a SBA (sheep blood agar) plate which was incubated at 37° C. for 18 hours and examined to confirm uniform growth of one colony type. Viable counts were performed on final suspension by prepping saline in Eppendorf tubes (approximately 900 ul per tube), removing 100 µl sample and adding to first Eppendorf tube, vortexing the mixture and repeating using $2^{nd}$ Eppendorf tube containing saline. This process was continued for 5-6 tubes. Finally, 100 µl of $5^{th}$ and $6^{th}$ dilutions were plated out on plate count agar, incubated at 37° C. for 18 hours and colony counts performed to confirm that the CFU/ml was approximately $2.5 \times 10^8$.

Skin Wound Surgical Procedure

Figure 33:
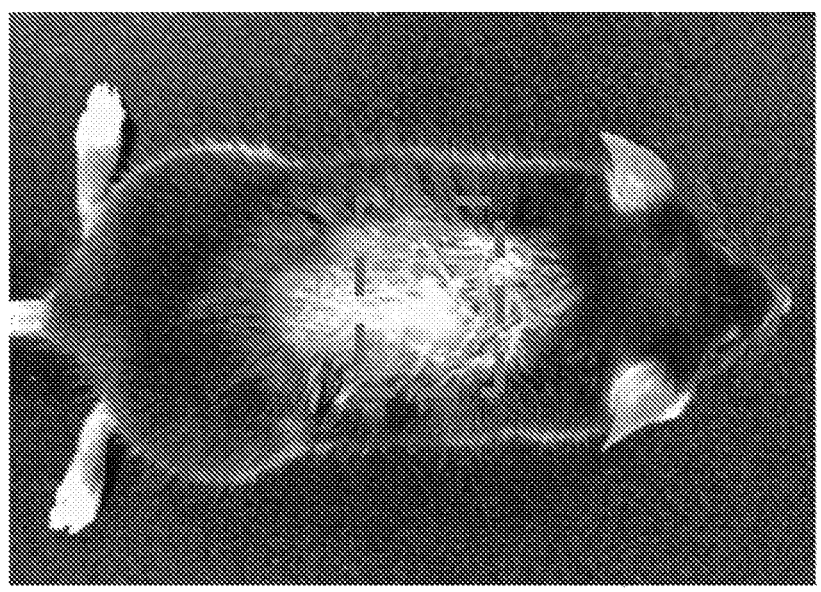
FIG. 33 is a photograph of an example of the shaved back skin hair from the surgical area of a mouse used in the murine studies of Example 5.

Each mouse was placed into induction chamber and anaesthesia induced using 2% isoflurane. Eyes of each anaesthetised mouse were covered with veterinary eye lubricant in order to prevent corneal dehydration. Each mouse removed from induction chamber and placed onto surgical area, in front of individual aesthetic nose cone. While under anaesthesia each mouse was monitored for assessment of depth of anaesthesia (response to pain, blink reflex, skeletal muscle tone) and respiratory and cardiac function. Back skin hair was shaved from surgical area (FIG. 33) with mechanical clippers. Shaved area was cleaned using 70% ethanol applied to paper towel followed by 10% w/v povidone-iodine solution. Once the iodine solution was dry, a subcutaneous injection of the nonsteroidal anti-inflammatroy agent meloxicam was administered. Dorsal skin was pinched gently to allow creation of a circular full-thickness wound using ear punch/biopsy punch. Vehicle control and LP1369 mice had wounds inoculated with 10 µl of bacterial suspension using a micropipette ($2.5 \times 10^6$ CFU/10 µl). Once the bacterial suspension was dry, mice were placed into individual recovery boxes labelled with the mouse number. The time of inoculation was recorded. Initial body weights of each mouse were recorded on the appropriate score sheet. Mice recovered to full consciousness within 5 minutes. Recovered mice were returned to individual housing and monitored hourly for post-surgical or anaesthetic complications.

Post-Surgical Care (6 Hours Post-surgery)

Mice were assessed for post-surgical complications and observations were recorded on clinic record sheet. Each mouse was carefully removed from IVC and placed into an assessment container, avoiding excessive handling or touching of the surgical site. Once the mouse was inside assessment container, it was assessed and the observations recorded on the post-surgical clinical record sheet. Whenever the suggested wellness breakpoints were reached, postoperative analgesia was administered and recorded on the clinical record sheet.

Animal Monitoring and Daily Care

Antibiotic Administration (7 am and 6 pm). The first administration of vehicle or LP1369 formulation (prepared in Example 4) occured 4 hours post-surgically. Each ointment container was weighted prior to administration and the weight recorded. Each mouse was carefully restrained. Ointment (vehicle or LP1369) was applied to the lesion area and the treated mouse was returned to IVC where each mouse was observed to ensure ointment was not immediately removed by grooming. The weight of the ointment container post-administration was recorded. The vehicle and active LP1369 products were applied to the skin wound each 12 hours following the first administration for a total of 11 consecutive treatments. The LP1369 product contained LP1369 at a concentration of 20 mg/g. Approximately 0.1-0.2 g of ointment was applied on each occasion, delivering a total topical dose of LP1369 between 22 and 44 mg to mice weighing between 21 g and 24 g.

Daily Monitoring. Monitoring of each mouse took place once daily at around 12 pm. Each mouse carefully removed from IVC and placed into observation container, avoiding excessive handling or touching surgical site. The coat, posture, eyes, behaviour, vocalisation and activity whilst in the container were carefully assessed and observations recorded on assessment sheet. Mouse faeces (either on floor of cage or in container) were checked for consistency and observations recorded. The weight of each mouse was determined whilst it was in the container and change in body weight calculated and recorded. Each mouse was placed onto the measurement grid and photographed. The observation container was disinfected with ethanol and set aside to dry while a fresh container was used for the next mouse.

Tissue Analysis and Assessment of Antibacterial Efficacy

At the end of the 6 day skin wound assessment period, all test mice were euthanized prior to wound collection for post mortem examination. The skin wound was dissected from the dorsum of each mouse. The sample was vortexed in a sample tube containing 1 ml PBS for approximately 30 seconds. 100 µl of supernatant was removed and placed into an Eppendorf tube containing 900 µl of PBS. This procedure was repeated using serial dilutions for a total of 8 dilutions. Finally, 100 µl of each dilution was pipetted onto a plate count agar in duplicate and incubated overnight at 37° C. Ten microlitres of original suspension was placed onto sheep blood agar to assess culture purity and incubated overnight at 37° C. The following day, viable counts were performed using incubated plate count agar plates and the identity of *Staphylococcus aureus* (the challenge organisms) as the harvested strain was confirmed.

Results

Figure 34B:
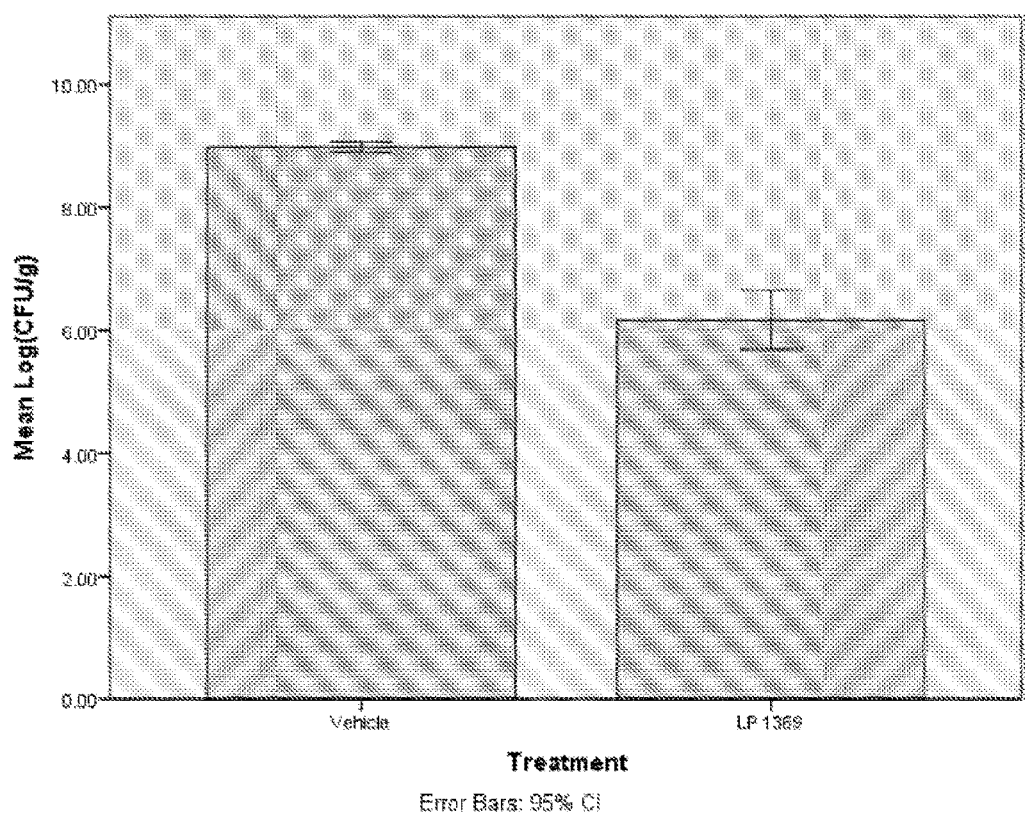

Viability testing of initial suspension demonstrated that mice were inoculated with approximately $3.0 \times 10^5$ CFU ($3.0 \times 10^7$ CFU/ml) with no statistically significant decrease in viability over the surgery time (p=0.5). The initial body weights of the animals was shown to be statistically similar across the treatment groups (vehicle v LP1369). As shown in FIGS. 34A-34B, the decrease in bacterial load of LP1369 treated mice compared to vehicle control mice was shown to be statistically significant.

Discussion

The microbiological results provide evidence that LP1369 formulated for topical use and applied to an induced skin infection in mice can reduce the bacterial population by greater than 99% (from a log CFU count per gram of infected tissue of 8.98 to a log count of 6.17 CFU/g). It is clearly demonstrated that LP1369 is biologically available to exert antibacterial activity against the challenge strain of *Staphylococcus aureus*. When developing a novel antibacterial agent for use in the treatment of topical bacterial infections, it is first necessary to determine the sensitivity of the target bacteria to the agent of interest (in this case LP1369) and then to demonstrate that the in vitro MIC results can be translated to effective biological activity in vivo. Both these important tests have now been successfully completed. Formulated LP1369 can now be further refined by modification of the dose regimen and formulation (using standard steps and methods available in the art) to provide an improved clinically useful treatment of topical microbial infection.

The invention claimed is:

1. A method of treating a topical bacterial infection in a subject, comprising administering topically a therapeutically effective amount of a polyether ionophore selected from the group consisting of: narasin, salinomycin, lasalocid, monensin, semduramicin, maduramicin, and laidlomycin, or a therapeutically acceptable salt thereof, and a chelating agent to the subject, wherein the bacteria is *Staphylococcus*, *Streptococcus*, *Propionibacterium* or *Pseudomonas*, wherein the step of administering topically is carried out by administering to the skin, nares, external ear canal or eye of the subject.

2. A method of preventing a topical bacterial infection in a subject, comprising administering topically therapeutically effective amount of a polyether ionophore selected from the group consisting of: narasin, salinomycin, lasalocid, monensin, semduramicin, maduramicin, and laidlomycin, or a therapeutically acceptable salt thereof, and a chelating agent to the subject, wherein the bacteria is *Staphylococcus*, *Streptococcus*, *Propionibacterium* or *Pseudomonas*, wherein the step of administering topically is carried out by administering to the skin, nares, external ear canal or eye of the subject.

3. The method according to claim 1, wherein the polyether ionophore, or the salt thereof, is administered to the subject at a concentration in the range of 5 μg/g to 900,000 mg/g.

4. The method according to claim 3, wherein the polyether ionophore, or the salt thereof, is administered to the subject at a dose within the range of 16 μg/g to 52 mg/g.

5. The method according to claim 1, wherein the bacteria is selected from the group consisting of: *Staphylococcus epidermidis, Staphylococcus simulans, Staphylococcus felis, Staphylococcus xylosus, Staphylococcus chromogenes, Staphylococcus warneri, Staphylococcus haemolyticus, Staphylococcus sciuri, Staphylococcus saprophyticus, Staphylococcus hominis, Staphylococcus caprae, Staphylococcus cohnii* subsp. *cohnii, Staphylococcus cohnii* subsp. *urealyticus, Staphylococcus capitis* subsp. *capitis, Staphylococcus capitis* subsp. *urealyticus, Staphylococcus hyicus, Staphylococcus aureus, Staphylococcus pseudintermedius, Staphylococcus delphini, Staphylococcus schleiferi* subsp. *coagulans, Staphylococcus aureus*subsp. *anaerobius, Streptococcus uberis, Streptococcus agalactiae, Streptococcus dysgalactiae, Streptococcus pyogenes, Streptococcus bovis, Streptococcus equi* subsp. *Zooepidemicus, Streptococcus equinus, Propionibacterium acnes, Propionibacterium granulosum,* and *Pseudomonas aeruginosa.*

6. The method according to claim 1, wherein the bacteria is antibiotic resistant.

7. The method according to claim 2, wherein the polyether ionophore, or salt thereof, is administered to the subject at a concentration in the range of 5 μg/g to 900,000 mg/g.

8. The method according to claim 7, wherein the polyether ionophore, or salt thereof, is administered to the subject at a dose within the range of 16 μg/g to 52 mg/g.

9. The method according to claim 2, wherein the bacteria is selected from the group consisting of: *Staphylococcus epidermidis, Staphylococcus simulans, Staphylococcus felis, Staphylococcus xylosus, Staphylococcus chromogenes, Staphylococcus warneri, Staphylococcus haemolyticus, Staphylococcus sciuri, Staphylococcus saprophyticus, Staphylococcus hominis, Staphylococcus caprae, Staphylococcus cohnii* subsp. *cohnii, Staphylococcus cohnii* subsp. *urealyticus, Staphylococcus capitis* subsp. *capitis, Staphylococcus capitis* subsp. *urealyticus, Staphylococcus hyicus, Staphylococcus aureus, Staphylococcus pseudintermedius, Staphylococcus delphini, Staphylococcus schleiferi* subsp. *coagulans, Staphylococcus aureus*subsp. *anaerobius, Streptococcus uberis, Streptococcus agalactiae, Streptococcus dysgalactiae, Streptococcus pyogenes, Streptococcus bovis, Streptococcus equi* subsp. *Zooepidemicus, Streptococcus equinus, Propionibacterium acnes, Propionibacterium granulosum,* and *Pseudomonas aeruginosa.*

10. The method according to claim 2, wherein the bacteria is antibiotic resistant.

11. The method according to claim 1, wherein the chelating agent is citric acid, EDTA or maltol.

12. The method according to claim 2, wherein the chelating agent is citric acid, EDTA or maltol.

\* \* \* \* \*